United States Patent
Shirasawa et al.

[11] Patent Number: 5,886,035
[45] Date of Patent: Mar. 23, 1999

[54] DIFLUOROPROSTAGLANDIN DERIVATIVES AND THEIR USE

[75] Inventors: Eiichi Shirasawa; Masaaki Kageyama; Tadashi Nakajima, all of Ikoma; Takashi Nakano, Yokohama; Nobuaki Mori, Yokohama; Hideshi Sasakura, Yokohama; Yasushi Matsumura, Yokohama; Yoshitomi Morizawa, Yokohama, all of Japan

[73] Assignees: Asahi Glass Company Ltd., Tokyo, Japan; Santen Pharmaceutical Co., Ltd., Osaka, Japan

[21] Appl. No.: 993,017

[22] Filed: Dec. 18, 1997

[30] Foreign Application Priority Data

Dec. 26, 1996 [JP] Japan .................................. 8-348614
Mar. 26, 1997 [JP] Japan .................................. 9-074054
Jun. 27, 1997 [JP] Japan .................................. 9-172477

[51] Int. Cl.$^6$ ..................... C07C 405/00; A61K 31/557
[52] U.S. Cl. ...................... 514/330; 514/573; 510/121; 562/503
[58] Field of Search ................. 560/121; 502/503; 514/530, 573

[56] References Cited

U.S. PATENT DOCUMENTS 5,166,178  11/1992  Ueno ........................................ 514/573

*Primary Examiner*—Robert Gerstl
*Attorney, Agent, or Firm*—Oblon, Spivak, McClelland, Maier & Neustadt, P.C.

[57] ABSTRACT

A fluorine-containing prostaglandin derivative of the formula (1) (or a salt thereof) and a medicine containing it, particularly, a preventive or therapeutic medicine for an eye disease:

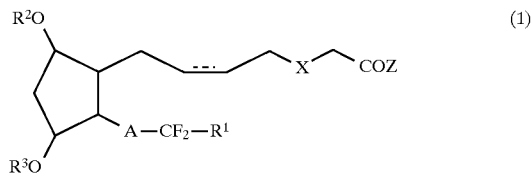

wherein A is a vinylene group or the like, $R^1$ is an aryloxyalkyl group or the like, $R^2$ and $R^3$ are hydrogen atoms or the like, and Z is $OR^4$ (wherein $OR^4$ is a hydrogen atom or an alkyl group) or the like.

14 Claims, No Drawings

DIFLUOROPROSTAGLANDIN DERIVATIVES AND THEIR USE

The present invention relates to fluorine-containing prostaglandin derivatives having two fluorine atoms at the 15-position (or their salts) and medicines containing the compounds as an active ingredient, particularly, preventive or therapeutic medicines for eye diseases.

The naturally occurring prostaglandins (PGs) are a class of biologically active substances synthesized in the body and cellular functions in various tissues of the body as local hormones having various biological activities. The PGs F, a group of naturally occurring PGs, are known to lower intraocular pressure when topically applied to the eye and are expected to find applications as therapeutic medicines for ocular hypertension or glaucoma (U.S. Pat. No. 4,599,353). However, they are irritant to the eye and have a problem of their inflammatory side effects such as congestion and damage to the cornea. Therefore, research for development of PGF derivatives which do not have such side effects is extensively conducted both at home and abroad. PGF derivatives having a cyclic structure in the ω-chain are also known. Shielnshantz et al. reported specific PGA, PGB, PGD, PGE and PGF derivatives modified by introduction of a cyclic structure are less irritant and congestive to the eye (Japanese Unexamined Patent Publication JP-A-8-109132). Ophthalmic compositions for local therapeutic medicines for glaucoma and ocular hypertension containing a chloroprostenol or fluprostenol analog have been also reported (Japanese Unexamined Patent Publication JP-A-7-165703).

Among the above-mentioned compounds disclosed in the literature, the compound 13,14-dihydro-17-phenyl-18,19,20-trinor-PGF$_{2\alpha}$ isopropyl ester (Latanoprost) has an excellent pharmacological effect, and ophthalmic solutions containing Latanoprost as an active ingredient are used for treatment of glaucoma and ocular hypertension at actual medical sites. Although Latanoprost is less irritant and congestive to the eye, there is still room for improvement in the melanogenesis-stimulating property and the duration of efficacy. In particular, Latanoprost stimulates melanogenesis, and its side effect of causing iridal pigmentation (A. Alm, et al, Ophthalmology, Vol. 102, No. 12, 1743–1752 (1995)) remains a problem to be solve.

For this reason, extensive research has been conducted both at home and abroad for development of long-lasting PGF derivatives having much the same biological activities as the naturally occurring one and few side effects.

Meanwhile, Bezglov et al. reported 15-fluoro-15-deoxy PGF$_{2\alpha}$, which is derived from naturally occurring PGF2α by introducing fluorine at the 15-position and retains the skeleton of its origin. 15-Fluoro-15-deoxy-PGF$_{2\alpha}$ is reported to have remarkable pharmacological actions such as the 100-fold greater contraction action and the 1000-fold relaxation action on smooth muscle in the respiratory system as compared with those of the naturally occurring PGF$_{2\alpha}$ and the action on the smooth muscle in the digestive and circulatory systems comparable to that of the naturally occurring PGF$_{2\alpha}$ (Izv. Akad. Nauk SSSR, Ser. Biol., 6,831 (1989)). However, no report has been made on any pharmacological actions of the compound on any eye disease, particularly on glaucoma.

No prostaglandin F derivatives that have a fluorine atom at the 15-position have been known except 15-fluoro-15-deoxy-PGF$_{2\alpha}$. Especially, no report has been made on derivatives having two fluorine atoms at the 15-position, 15,15-difluoro-15-deoxy PGs F$_{2\alpha}$ per se or their synthesis.

The present inventors synthesized 15,15-difluoro-15-deoxy-PGF$_{2\alpha}$ and its novel derivatives and measured their biological activities to assess their usefulness as medicines. The present inventors also measured the biological activities of derivatives of 15,15-difluoro-15-deoxy-PGF$_{2\alpha}$ which have a substituted or unsubstituted aryloxy group on the ω-chain and are prepared by modifying the carboxyl group or the hydroxyl group of the prostaglandin to assess their usefulness as medicines. As a result, the present inventors have found that 15,15-difluoro-15-deoxy-PGF$_{2\alpha}$ and its derivatives are superior to the known natural PGF$_{2\alpha}$ in the effect of lowering intraocular pressure are scarcely irritant to the eye, scarcely affect the ocular tissues such as the cornea, the iris and the conjunctive, and have long-lasting efficacy. They are characterized in that they stimulates melanogenesis much less as well as in that their efficacy lasts longer than Latanoprost.

The present invention relates to the compound 15,15-difluoro-15-deoxy-PGF$_{2\alpha}$ and its derivatives and their use as medicines, in particular, as medicines for eye diseases, and provides a fluorine-containing prostaglandin derivative of the following formula (1) or a salt thereof:

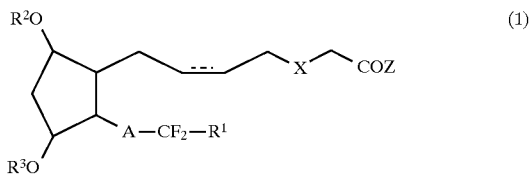

(1)

wherein A is an ethylene group, a vinylene group, an ethynylene group, —OCH$_2$— or —SCH$_2$—, R$^1$ is a substituted or unsubstituted C$_{3-8}$ alkyl group, a substituted or unsubstituted C$_{3-8}$ alkenyl group, a substituted or unsubstituted C$_{3-8}$ alkynyl group, a substituted or unsubstituted C$_{3-8}$ cycloalkyl group, a substituted or unsubstituted aralkyl group or a substituted or unsubstituted aryloxyalkyl group, each of R$^2$ and R$^3$ which are independent of each other, is a hydrogen atom or an acyl group, or forms a single bond together with Z, X is —CH$_2$—, —O— or —S—, Z is —OR$^4$, —NHCOR$^5$, —NHSO$_2$R$^6$ or —SR$^7$, or forms a single bond together with R$^2$ or R$^3$, each of R$^4$, R$^5$, R$^6$ and R$^7$ which are independent of one another, is a hydrogen atom, an alkyl group, an alkenyl group, an alkynyl group, a cycloalkyl group, an aryl group or an aralkyl group, and a dual line consisting of solid and broken lines is a single bond, a cis-double bond or a trans-double bond, a medicine containing the above compound as an active ingredient; and a preventive or therapeutic medicine for an eye disease containing the above compound as an active ingredient.

The fluorine-containing prostaglandin derivatives of the present invention may be the same as the naturally occurring type except for the two fluorine atoms at the 15-position (namely, compounds wherein A is a vinylene group, R$^1$ is a n-pentyl group, both R$^2$ and R$^3$ are hydrogen atoms, X is —CH$_2$—, Z is —OH, and the dual line is a cis-double bond). However, among the fluorine-prostaglandin derivatives of the present invention, those having an ω-chain which is not of the naturally occurring type (namely, wherein A is a vinylene group, and R$^1$ is a n-pentyl group) are preferred. In particular, those having wherein R$^1$ is one of the above-mentioned groups except an alkyl group are preferred.

In the present invention, the eye disease as the target for prevention or therapy is preferably glaucoma or ocular hypertension.

In the following description, the term "lower" for an organic group corresponds to a carbon number of from 1 to 6. A preferred lower organic group is an organic group having from 1 to 4 carbon atoms.

An "alkyl group" may be linear or branched, and unless otherwise noted, a lower alkyl group is preferred. Specific examples include a methyl group, an ethyl group, a propyl group, an isopropyl group, a butyl group, an isobutyl group, a sec-butyl group, a t-butyl group, a pentyl group and a hexyl group.

An "alkenyl group" is preferably a lower alkenyl group, unless otherwise noted, and more preferably a linear or branched alkenyl group having from 2 to 6 carbon atoms and one unsaturated group. Specific examples include a vinyl group, an allyl group, a 1-propenyl group, an isopropenyl group, a 3-butenyl group, a 3-pentenyl group and a 4-hexenyl group.

An "alkynyl group" is preferably a lower alkynyl group, unless otherwise noted, more preferably a linear or branched alkynyl group having from 2 to 6 carbon atoms and one unsaturated group. Specific examples include a 1-propynyl group, a 2-propynyl group, a 3-butynyl group, a 3-pentynyl group and a 4-hexynyl group.

As an "alkoxy group", although a wide variety of common alkoxy groups may be used, a lower alkoxy group is preferred, and more preferred is a linear or branched alkoxy group having from 1 to 4 carbon atoms. Specific examples include a methoxy group, an ethoxy group, a propoxy group and a butoxy group.

A "halogen atom" means a fluorine atom, a chlorine atom, a bromine atom or an iodine atom.

An "aryl group" means a monovalent aromatic hydrocarbon group which may have a substituent (such as a lower alkyl group, a halogen atom, a haloalkyl group, a lower alkoxy group or a lower alkylamino group), preferably a phenyl group or its derivative. For example, a phenyl group, a tolyl group, a halophenyl group (such as a chlorophenyl group, a fluorophenyl group or a bromophenyl group), a dihalophenyl group (such as a dichlorophenyl group, a difluorophenyl group or a dibromophenyl group), a trihalophenyl group (such as a trichlorophenyl group, a trifluorophenyl group or a tribromophenyl group), a haloalkylphenyl group (such as a trifluoromethylphenyl group), an alkoxyphenyl group (such as a methoxyphenyl group or an ethoxyphenyl group), a dialkoxyphenyl group (such as a dimethoxyphenyl group or a diethoxyphenyl group) or a trialkoxyphenyl group (such as a trimethoxyphenyl group or a triethoxyphenyl group) may be mentioned.

An "aralkyl group" means an aryl-substituted alkyl group, in which the aryl group as the substituent may be as described above, and the carbon number of the alkyl group is preferably from 1 to 4. Specific examples include a benzyl group, a benzhydryl group, a trityl group and a phenethyl group.

A "cycloalkyl group" means an unsubstituted or substituted 3 to 8-membered cycloalkyl group, and when substituted, may have a lower alkyl group, a halogen atom or an alkoxy group as a substituent. For example, a cyclopropyl group, a cyclobutyl group, a cyclopentyl group, a cyclohexyl group, a cycloheptyl group, a methylcyclohexyl group, a dimethylcyclopentyl group, a dimethylcyclohexyl group, a chlorocyclohexyl group or a dichlorocyclohexyl group may be mentioned.

A "haloalkyl group" means a lower haloalkyl group having at least one halogen atom. A fluoromethyl group, a difluoromethyl group, a trifluoromethyl group, a trifluoroethyl group, a pentafluoroethyl group, a chloromethyl group, a dichloromethyl group, a trichlromethyl group or a bromomethyl group may be mentioned.

An "acyl group" means a monovalent or polyvalent group derived from a carboxylic acid by removing hydroxyl group (s) from all the carboxyl group(s). As the carboxylic acid, a saturated or unsaturated aliphatic carboxylic acid, a carbocyclic carboxylic acid or a heterocyclic carboxylic acid may be mentioned. As the carbocyclic carboxylic acid, a saturated or unsaturated alicyclic carboxylic acid or an aromatic carboxylic acid may be mentioned.

Among the fluorine-containing prostaglandin derivatives of the formula (1) (hereinafter referred to as the fluorine-containing prostaglandin derivatives (1)), the following compounds are preferred from the standpoint of biological activities and physical properties.

As A, a vinylene group or an ethylene group is preferred, and the vinylene group induces cis- or trans-vinylene groups. A trans-vinylene group is particularly preferred. In the case of —OCH$_2$— or —SCH$_2$—, the oxygen atom or the sulfur atom is preferably linked to the ring.

As X, —CH$_2$— is particularly preferred.

The dual line consisting of solid and broken lines is preferably a cis-double bond.

$R^1$ is preferably an organic group corresponding to the ω-chain moiety of the naturally occurring $PGF_{2\alpha}$ (when the rest is not of the naturally occurring type) or an organic group corresponding to the ω-chain moiety of any of various synthetic PGs $F_{2\alpha}$. Such organic groups include, for example, a $C_{3-8}$ alkyl group, a $C_{3-8}$ alkenyl group, a $C_{3-8}$ alkynyl group, a $C_{3-8}$ cycloalkyl group, an aralkyl group, an aryloxy group having an aryl group such as a phenyl group, and such groups having various substituents.

The alkyl group may have a cyclic organic group such as a cycloalkyl group as a substituent, and the alkenyl group and the alkynyl group may have a cyclic organic group such as an aryl group or a cycloalkyl group as a substituent. For example, $R^1$ may be a cycloalkyl group-substituted alkyl group, a cycloalkyl group-substituted alkenyl group, or an aryl group-substituted alkenyl group. Further, it may be an organic group having an oxygen atom or a sulfur atom introduced to replace a carbon atom of a linear organic group such as an alkyl group, or an organic group having a cyclic organic group such as a cycloalkylene group or an arylene group introduced between two carbon atoms of a linear organic group. Further, a cycloalkyl group, an aralkyl group, an aryloxy group and an organic group having such a group as a substituent may have a linear organic group such as an alkyl group as a substituent on the ring moiety. Substituents in $R^1$ include, in addition to the above-mentioned substituents, a halogen atom, an oxygen atom-containing substituent, a sulfur atom-containing substituent, a nitrogen atom-containing substituent, and others.

When $R^1$ is a linear substituted or unsubstituted group, a linear $C_{5-6}$ alkyl group, a linear $C_{5-6}$ alkenyl group and a linear $C_{5-6}$ alkynyl group and such groups substituted with one or two methyl group are particularly preferred. Specific linear groups as $R^1$ include the following groups. Among them, preferred are a n-pentyl group, a 2-methylhexyl group, a 1-methyl-3-pentynyl group, a 1-methyl-3-hexynyl group, and a 1,1-dimethyl-3-hexynyl group.

A n-propyl group, a n-butyl group, a n-pentyl group, a n-hexyl group, a n-heptyl group, a n-octyl group, a n-decyl group, a 1-methylpentyl group, a 1,1-dimethylpentyl group, a 1-methylhexyl group, a 2-methylpentyl group, a 2-methylhexyl group, a 3-pentenyl group, a 1-methyl-3-pentenyl group, a 1-methyl-3-hexenyl group, a 1,1-dimethyl-3-pentenyl group, a 1,1-dimethyl-3-hexenyl group, a 2-methyl-3-pentenyl group, a 2-methyl-3-hexenyl group, a 3-pentynyl group, a 1-methyl-3-pentynyl group, a 1-methyl-3-hexynyl group, a 2-methyl-3-pentynyl group, a 2-methyl-3-hexynyl group, a 1,1-dimethyl-3-pentynyl group, and a 1,1-dimethyl-3-hexynyl group.

The substituted or unsubstituted cycloalkyl group as $R^1$ is preferably a $C_{3-8}$ cycloalkyl group, or such a cycloalkyl group substituted by at least one lower alkyl group. Particularly preferred is an unsubstituted cyclopentyl group, an unsubstituted cyclohexyl group, a $C_{1-4}$ alkyl group-substituted cyclopentyl group, or a $C_{1-4}$ alkyl group-substituted cyclohexyl group.

The substituted or unsubstituted aralkyl group as $R^1$ is preferably an aralkyl group which contains, for example, a benzene ring, a furan ring, a thiophene ring or a naphthalene ring and may be substituted by, for example, a halogen atom, a haloalkyl group, an alkoxy group or a hydroxyl group. The carbon number of the alkyl moiety (i.e. the alkylene group) of the aralkyl group is preferably from 1 to 4. A particularly preferred aralkyl group is a $C_{1-2}$ alkyl group substituted with a phenyl group or a $C_{1-2}$ alkyl group substituted with a phenyl group substituted with one or two lower alkyl groups.

Specifically, a phenylmethyl group, a 2-phenylethyl group, a 3-methylphenylmethyl group, a 2-(3-methylphenyl) ethyl group, a 3-trifluoromethylphenylmethyl group, a 2-(3-trifluoromethylphenyl)ethyl group, a 3-chlorophenylmethyl group, a 2-(3-chlorophenyl)ethyl group, a 2-(3,5-dichlorophenyl)ethyl group and a 2-(3,4-dichlorophenyl) ethyl group are preferred.

The substituted or unsubstituted aryloxyalkyl group as $R^1$ is preferably an aryloxyalkyl group which contains, for example, a benzene ring, a furan ring, a thiophene ring or a naphthalene ring and may have, for example, a halogen atom, a haloalkyl group, an alkoxy group or a hydroxyl group as a substituent on the aryl moiety. The aryl moiety is preferably a phenyl group which is not substituted or substituted with from 1 to 3 halogen atoms or haloalkyl groups. The carbon number of the alkyl moiety substituted with an aryloxy group is preferably from 1 to 3.

Specific preferred aryloxyalkyl groups as a phenoxymethyl group, a 3-chlorophenoxymethyl group, a 3-fluorophenoxymethyl group, a 3-trifluoromethylphenoxymethyl group, a 3,5-dichlorophenoxymethyl group, a 3,4-dichlorophenoxymethyl group, a 3,5-difluorophenoxymethyl group, a 3,4-difluorophenoxymethyl group, a 3,5-bis(trifluoromethyl)phenoxymethyl group and a 3,4-bis(trifluoromethyl)phenoxymethyl group.

As $R^1$, in addition to those described above, a $C_{1-4}$ alkyl group substituted by the above-mentioned cycloalkyl group is preferred as a type of substituted alkyl group. As such a cycloalkyl group, a cyclopentyl group or a cyclohexyl group is preferred, and as such an alkyl group, a $C_{1-2}$ alkyl group is preferred. Specific examples include a cyclopentylmethyl group, a 2-cyclopentylethyl group and a cyclohexylmethyl group.

As $R^1$, more preferred are the above-mentioned substituted or unsubstituted aryloxyalkyl groups. Among them, a substituted or unsubstituted phenoxymethyl group such as a phenoxymethyl group, a 3-chlorophenoxymethyl group, a 3,5-dichlorophenoxymethyl group or a 3,4-dichlorophenoxymethyl group is preferred.

Each of $R^2$ and $R^3$ which are independent of each other, is a hydrogen atom or an acyl group, or forms a single bond as described later. It is preferred that both $R^2$ and $R^3$ are hydrogen atoms, or that either $R^2$ or $R^3$ is an acyl group and the other is a hydrogen atom. When only one of them is an acyl group, it is preferred that $R^2$ is an acyl group. Compounds wherein at least one of $R^2$ and $R^3$ is an acyl group are useful as prodrugs because they hydrolyze in vivo to biologically active compounds. As the acyl group, a $C_{2-20}$ acyl group, particularly, an aliphatic hydrocarbon type $C_{2-20}$ acyl group is preferred. In particular, fluorine-containing prostaglandin derivatives wherein either $R^2$ or $R^3$ is an aliphatic linear hydrocarbon type acyl group having a carbon number of at least 4 are useful as prodrugs having improved lipid solubility.

Z is $—OR^4$, $—NHCOR^5$, $—NHSO_2R^6$, $—SR^7$ or represents a single bond together with $R^2$ or $R^3$, which means cyclization of a compound wherein Z is OH and either $R^2$ or $R^3$ is a hydrogen atom (a compound having a carboxyl group at the end of the α-chain and a hydroxyl group either at the 9-position or at the 11-position) by esterification of the carboxyl group and the hydroxyl group to form an ester bond between the end of the α-chain and the 9- or 11-position. Such cyclic compounds having an ester bond hydrolyze in vivo into biologically active compounds, and therefore are useful as prodrugs.

As $R^4$–$R^7$ in the groups represented by $—OR^4$, $—NHCOR^5$, $—NHSO_2R^6$ and $—SR^7$, a hydrogen atom, an alkyl group, an alkenyl group, an alkynyl group, a cycloalkyl group, an aryl group and an aralkyl group may be mentioned. The alkyl group, the alkenyl group, the alkynyl group and the alkyl moiety of the aralkyl group may be linear or branched and may have various substituents such as halogen atoms. The cycloalkyl group, the aryl group and the aralkyl group may have an alkyl group or other substituents on the ring. As such substituents, the substituents described above for $R^1$ may be mentioned.

The alkyl group, the alkenyl group and the alkynyl group as $R^4$–$R^7$ preferably have a carbon number of at most 20, particularly, at most 8. Specific examples of these linear hydrocarbon groups include the following groups. As the alkyl group, a methyl group, an ethyl group, a n-propyl group, an isopropyl group, a n-butyl group, a n-pentyl group, a n-hexyl group, a n-heptyl group, a n-octyl group, a n-decyl group, a 1-methylpentyl group, a 1,1-dimethylpentyl group, a 1-methylhexyl group, a 2-methylpentyl group and 2-methylhexyl group may be mentioned.

As the alkenyl group, an allyl group, a 2-butenyl group, a 3-pentenyl group, 1-methyl-3-pentenyl group, 1-methyl-3-hexenyl group, 1,1-dimethyl-3-pentenyl group and a 1,1-dimethyl-3-hexenyl group may be mentioned.

As the alkenyl group, a propargyl group, a 3-pentynyl group, a 1-methyl-3-pentynyl group, a 1-methyl-3-hexynyl group, a 1,1-dimethyl-3-pentynyl group and a 1,1-dimethyl-3-hexynyl group may be mentioned.

As the substituted alkyl group, a halogen atom-substituted alkyl group or a cycloalkyl group-substituted alkyl group may be mentioned. The carbon number of the halogen atom-substituted alkyl group is preferably at most 6, and the carbon number of the alkyl moiety of the cycloalkyl group-substituted alkyl group is preferably from 1 to 2. As the halogen atom-substituted alkyl group, for example, a trifluoromethyl group or a pentafluoroethyl group may be mentioned. As the cycloalkyl group-substituted alkyl group, for example, a cyclobutylmethyl group, a cyclopentylmethyl group or a cyclohexylmethyl group may be mentioned.

The carbon number of the cycloalkyl group is preferably at most 10. Specific examples include a cyclopropyl group, a cyclobutyl group, a cyclopentyl group, a cyclohexyl group, a 2,2-dimethylcyclopropyl group, a 3-cyclopentenyl group, a 3-cyclohexynyl group and a cyclooctanyl group.

As the aryl group, a substituted or unsubstituted phenyl group is preferred. As the substituent, an alkyl group (preferably having a carbon number of at most 4), a halomethyl group, a halogen atom, an alkoxy group, an acyl group, an acylamino group or a nitro group is preferred. Specific examples of the aryl group include a phenyl group, a 4-methylphenyl group, a 4-(t-butyl)phenyl group, a 3-trifluoromethylphenyl group, a 4-trifluoromethylphenyl group, a 4-chlorophenyl group, a 4-acetylphenyl group, a 4-benzoylphenyl group, a 4-acetylaminophenyl group, a 4-benzoylaminophenyl group, a 3-nitrophenyl group and a 4-nitrophenyl group.

As the aralkyl group, an aralkyl group consisting of an alkyl moiety having a carbon number of at most 4 (preferably a carbon number of 1 or 2) and a phenyl group is preferred. The phenyl group may be substituted with an alkyl group (preferably having a carbon number of at most 4), a halomethyl group, a halogen atom, an alkoxy group, an acyl group, an acylamino group, a nitro group or the like. The alkyl moiety of the aralkyl group may be branched. Specific examples include:

a benzyl group, a phenethyl group, a diphenylmethyl group, a 3-methylphenylmethyl group, a 3-chlorophenylmethyl group, a 3-fluoromethylphenylmethyl group, a 3-bromophenylmethyl group, a 3-trifluoromethylphenylmethyl group, a 1-(3-methylphenyl)ethyl group, a 1-(3-chlorophenyl)ethyl group, a 1-(3-trifluoromethylphenyl)ethyl group, a 1-(3-fluorophenyl)ethyl group, a 1-(3-bromophenyl)ethyl group, a 2-(3-methylphenyl)ethyl group, a 2-(3-chlorophenyl)ethyl group, a 2-(3-trifluoromethylphenyl)ethyl group, a 2-(3-fluorophenyl)ethyl group, a 2-(3-bromophenyl)ethyl group, a 1-methyl-2-(3-methylphenyl)ethyl group, a 1-methyl-2-(3-chlorophenyl)ethyl group, a 1-methyl-2-(3-trifluoromethylphenyl)ethyl group, a 1-methyl-2-(3-fluorophenyl)ethyl group and a 1-methyl-2-(3-bromophenyl)ethyl group.

Each of $R^4$–$R^7$ is preferably a substituted or unsubstituted alkyl, cycloalkyl or aralkyl group. As the substituent, a halogen atom or an alkyl group having a carbon number of at most 4 which is bonded to a ring is preferred. Particularly preferred $R^4$–$R^7$ are alkyl groups, and a haloalkyl is particularly preferred as $R^6$.

Z is preferably a group represented by —$OR^4$. $R^4$ in Z is preferably a hydrogen atom or a $C_{1-20}$ hydrocarbon group such as an alkyl group, a cycloalkyl group or an aralkyl group. Compounds wherein $R^4$ is a hydrocarbon group are useful as prodrugs because they hydrolyze in vivo into biologically active compounds. It is possible to improve the lipid solubility of compounds by proper selection of hydrocarbon groups. As Z, particularly preferred are a hydroxyl group, a methoxy group, an ethoxy group, an isopropoxy group, an isobutoxy group, a cyclohexyloxy group and a benzyloxy group.

A fluorine-containing prostaglandin derivative of the present invention having an acidic group such as a carboxy group, for example like those wherein Z is a hydroxyl group, may take the form of a salt with a base. Similarly, when a compound of the present invention has a basic group such as an amino group, it may take the form of a salt with an acid. Salts with bases include alkali metal salts such as sodium salts and potassium salts, alkaline earth metal salts such as calcium salts and magnesium salts and ammonium salts such as unsubstituted ammonium salts and alkyl-substituted ammonium salts. Salts with acids include inorganic acid salts such as hydrochlorides, sulfates and phosphates and organic acid salts such as acetates, oxalates, citrates, succinates and p-toluenesulfonates.

The fluorine-containing prostaglandin derivatives of the present invention can be synthesized by a process similar to a general process for producing prostaglandin $F_{2\alpha}$. For example, first of all, the ω-chain is introduced into the starting material, a Corey lactone, and the resulting enone is converted by fluorination into an ω-chain-containing Corey lactone having two fluorine atoms at the 15-position. Subsequent reduction of the lactone is to a lactol followed by introduction of the α-chain unit by the Wittig reaction, and, if necessary, acylation or of a hydroxyl group or removal of the protecting group for a hydroxyl group, gives fluorine-containing prostaglandin derivatives of the present invention. The introduction of the α-chain unit may be followed by conversion of a carboxyl group into an ester, an acyl amide, a sulfonamide or a thioester and, if necessary, removal of the protecting group for a hydroxyl group or acylation of a hydroxyl group to produce fluorine-containing prostaglandin derivatives of the present invention.

Specifically speaking, the fluorine-containing prostaglandin derivatives (1) can be prepared, for example, by a process comprising fluorination of a ketone (2) having an ω-chain to give an ω-chain-containing Corey lactone (3) having two fluorine atoms at the 15-position, reduction of the lactone (3) to a lactol (4) and reaction of the lactol (4) with a phosphorane (5) to introduce an α-chain unit. The phosphorane (5) is obtainable from a phosphonium salt (6). Because it is not necessary for the starting compound to have the same configuration as the resulting fluorine-containing prostaglandin derivative (1), the following formulae (2) to (4) do not specify the configurations of the substituents bonded to the cyclopentane rings. In the formulae (5) and (6), $R^8$ is a substituted or unsubstituted alkyl group, a substituted or unsubstituted aryl group, a substituted or unsubstituted aralkyl group or a dialkylamino group, and Y is a halogen atom such as a chlorine atom, a bromine atom or an iodine atom.

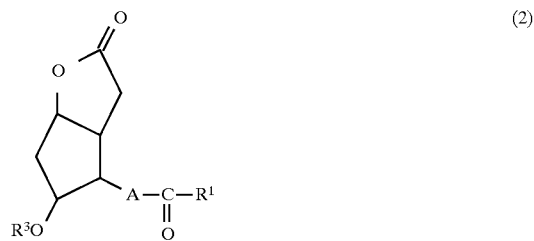

(2)

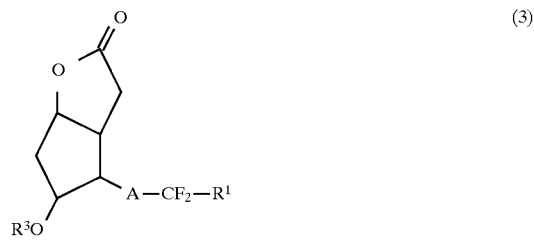

(3)

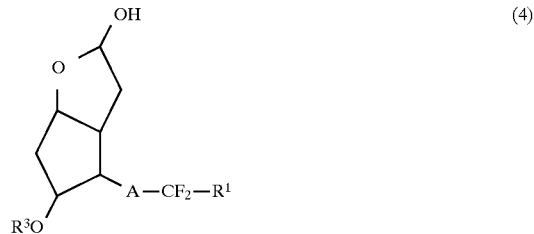

(4)

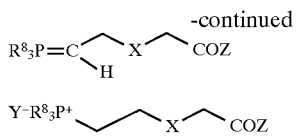

The ketones shown above are known compound except those having specific substituents as $R^1$. The novel ketones having specific substituents as $R^1$ can be prepared by a process similar to that for the other known ketones. For example, these ketones can be prepared by reaction of a dialkyl 3-substituted-2-oxopropylphosphonate with a Corey lactone having a formyl group.

The conversion of a ketone into an ω-chain-containing Corey lactone having two fluorine atoms at the 15-position by fluorination can be achieved by various known fluorination processes, for example, by using various nucleophilic fluorinating agents in inert solvents.

When a ketone as the starting material has a functional group liable to fluorinate during the fluorination, it is preferred to preliminarily protect the functional group by a protecting group. For example, when $R^3$ is a hydrogen atom, $R^3$ is preferably protected by a protecting group during the fluorination of the carbonyl group at the 15-position and then the protection group is removed.

The protecting groups include, for example, a triorganosilyl group, an acyl group, an alkyl group, an aralkyl group and a cyclic ether group. An acyl group to protect a hydroxyl group at the 11-position of a ketone used as the starting material may be the same as or different from the acyl group as $R^3$ of a fluorine-containing prostaglandin derivative (1). A fluorine-containing prostaglandin derivative (1) having an acyl group which is different from the acyl group used as the protecting group can be obtained by removing the protecting group and then introducing a different acyl group.

The triorganosilyl group is a group having three organic groups such as alkyl groups, aryl groups, aralkyl groups or alkoxy groups bonded to a silicon atom. Particularly preferred is a triorganosilyl group having three groups of at least one kind selected from the group consisting of lower alkyl groups and aryl groups. Specifically, a t-butyldimethylsilyl group, a t-butyldiphenylsilyl group, a triethylsilyl group, a triphenylsilyl group or a triisopropylsilyl group may, for example, be preferred.

As the acyl group, an acetyl group, a trifluoroacetyl group, a pivaloyl group, a benzoyl group or a p-phenylbenzoyl group is preferred, and as the cyclic ether group, a tetrahydropyranyl group or a tetrahydrofuranyl group is preferred. As the alkyl group or the aralkyl group which may have a substituent, an alkoxyalkyl group such as a methoxymethyl group, a 1-ethoxyethyl group or a 2-methoxyethoxymethyl group as well as a benzyl group, a methoxybenzyl group or a trityl group may, for example, be mentioned.

The protecting group for a hydroxyl group as mentioned above, can be converted to a hydroxyl group by a conventional method. For example, it can readily be converted to a hydroxyl group by methods disclosed in publications e.g. "Shinjikken Kagaku Koza 14 Syntheses and Reactions of Organic Compounds (I), (II) and (V)", published by Maruzen, and "Protective Groups in Organic Synthesis" written by T. W. Greene, published by J. Wiley & Sons.

The process for fluorination of a ketone having a carbonyl group at the 15-position as the starting material to an ω-chain-containing Corey lactone having two fluorine atoms at the 15-position uses a fluorinating agent. The fluorination is preferably carried out in an inert solvent and may be conducted in the presence of a base. The reaction temperature for the fluorination is usually from −150 to +100° C., preferably from −80 to +60° C. A fluorinating agent is used usually in an amount of from 0.5 to 20 parts by weight, preferably from 1 to 5 parts by weight, per part by weight of the substrate, a ketone as the starting material. The fluorinating agent used in the process for fluorinating a ketone having a carbonyl group at the 15-position as the starting material to an ω-chain-containing Corey lactone having two fluorine atoms at the 15-position is not particularly limited, and known or common nucleophilic fluorinating agents may be employed. For example, nucleophilic fluorinating agents disclosed in publications such as "Fluorine Chemistry" written by Tomoya Kitazume, Takashi Ishihara and Takeo Taguchi and published by Kodansha Scientific, may be used.

Specifically, dialkylaminosulfur trifluoride derivatives, tetrafluorophenylphophorane, fluoroalkylamine agents such as diethylamine-chlorotrifluoroethene adducts and diethylamine-hexafluoropropene adducts, hydrogen fluoride-amine complexes such as HF-pyridine and HF-triethylamine, silicon tetrafluoride, sulfur tetrafluoride, metal fluorides such as potassium fluoride, cesium fluoride and silver fluoride, and ammonium salts and phosphonium salts such as tetrabutylammonium fluoride, tetraethylammonium fluoride and tetrabutylphosphonium fluoride may, for example, be mentioned.

A carbonyl group can directly be fluorinated by using these nucleophilic fluorinating agents. A carbonyl group may be fluorinated after conversion of a ketone into its derivative such as an oxime, a hydrazone, a thioacetal or a diazo compound in order to improve its reactivity or inhibit side reactions. For example, the process of Olah et al. (Synlett 1990, 594, Synlett 1994, 425), the process of Katzenellenbogen et al. (J. Org. Chem. 51, 3508 (1986)), the process of Hiyama et al. (Synlett 1991, 909) and the process of Fujisawa et al. (J. Fluorine Chem. 71, 9 (1995)) are applicable.

Fluorination of a carbonyl group by a nucleophilic fluorinating agent is preferred in view of yield and selectivity. Dialkylaminosulfur trifluoride derivatives are particularly preferred as the nucleophilic fluorinating agent for fluorination, and specifically, morpholinosulfur trifluoride, piperidinosulfur trifluoride, diethylaminosulfur trifluoride, dimethylaminosulfur trifluoride and the like are preferred. As the inert solvent, a halogen-containing solvent, an etherial solvent, a hydrocarbon solvent, an ester solvent, a polar solvent, a mixture thereof is preferred. An inert solvent is used usually in an amount of from 2 to 500 parts by weight, preferably from 5 to 100 parts by weight, per part by weight of a ketone.

Preferable halogen-containing solvents are methylene chloride, chloroform, 1,2-dichloroethane, carbon tetrachloride, chlorobenzene and dichloropentafluoropropanes.

Preferable etherial solvents are diethyl ether, tetrahydrofuran [THF], 1,4-dioxane, dimethoxyethane, diglyme and t-butyl methyl ether.

Preferable hydrocarbon solvents are hexane, toluene, benzene, pentane, xylene and petroleum ether.

Preferable ester solvents are ethyl acetate and butyl acetate.

Preferable polar solvents are dimethyl sulfoxide, hexamethylphosphoramide [HMPA], 1,3-dimethyl-3,4,5,6-tetrahydro-2(1H)-pyrimidinone [DMPU], 1,3-dimethyl-2-imidazolidinone [DMI] and N,N,N',N'-tetramethylethylenediamine [TMEDA] (in the square brackets are abbreviations).

Particularly preferred solvents are methylene chloride, chloroform, 1,2-dichloroethane and toluene.

As the base used for the fluorination, amines such as tertiary amines and aromatic amines and salts of alkali metals and alkaline earth metals are preferred. Specifically, triethylamine, diisopropylethylamine, pyridine, 2,6-lutidine, dimethylaminopyridine, sodium carbonate, potassium carbonate, sodium hydrogencarbonate and potassium hydrogencarbonate may be mentioned.

The lactone obtained by the above-mentioned fluorination is reduced to a lactol. For the reduction, a reducing agent is usually used in an inert solvent. For example, methods disclosed in publications such as "Shinjikken Kagaku Koza 15 Oxidation and reduction (II)" published by Maruzen and "Jikken Kagaku Koza 26 Organic Syntheses VIII, asymmetric synthesis, reduction, sugar and labeled compounds, fourth edition" published by Maruzen may be used. In the reduction, a reducing agent is used usually in amount of from 0.01 to 50 equivalents, preferably from 1 to 20 equivalents, per equivalent of a lactone. The reaction temperature is preferably from −150° to +100° C., particularly preferably from −80° to 0° C.

As reducing agents, diisobutylaluminum hydride [DIBAH], dialkylaluminum alkoxides, lithium aluminum hydride, tributyltin hydride, triphenyltin hydride, triethylsilane, trichlorosilane, dimethylphenylsilane, diphenylsilane, sodium borohydride, sodium trimethoxyborohydride, lithium tri(s-butyl)borohydride, potassium tri(s-butyl)borohydride, lithium triethylborohydride, lithium trisiamylborohydride, potassium trisiamylborohydride, zinc borohydride, calcium borohydride, lithium trialkoxyaluminum hydrides, sodium bis(2-methoxyethoxy)aluminum hydride, diborane, disiamylborane, thexylborane and 9-borabiscyclo[3.3.1] nonane may be mentioned. Diisobutylaluminum hydride [DIBAH], sodium bis(2-methoxyethoxy)aluminum hydride, disiamylborane and lithium tri(s-butyl)borohydride are preferred.

As the inert solvent used for the reduction, an etherial solvent, a hydrocarbon solvent, a polar solvent or a mixture thereof is preferred. Specific examples of the etherial solvent, the hydrocarbon solvent and the polar solvent are the etherial solvents, hydrocarbon solvents and polar solvents specifically described above for the fluorination. Above all, diethyl ether, THF, t-butyl methyl ether and toluene are particularly preferred. The configuration of the lactol produced by the reduction is not particularly limited.

As described above, a phosphorane is produced from the corresponding phosphonium salt in an inert solvent in the presence of a base. The resulting phosphorane is not usually isolated and directly used for the Wittig reaction with a lactol. For production of a phosphorane from the corresponding phosphonium salt, methods disclosed in publications such as "Shinjikken Kagaku Koza 14 Syntheses and reactions of organic compounds (I)" published by Maruzen, and "Jikken Kagaku Koza 19 Organic Synthesis I, hydrocarbons and halogen compounds, fourth edition" published by Maruzen and the method of Schaaf et al. (J. Med. Chem. 22, 1340 (1979)) may, for example, be employed.

Z in the phosphorane or the phosphonium salt is usually a hydroxyl group (namely, $OR^4$ wherein $R^4$ is a hydrogen atom) although it may be any of those described above for Z. In such a case, the reaction of the phosphorane with lactol gives a fluorine-containing prostaglandin derivative wherein Z is a hydroxyl group. In order to obtain a fluorine-containing prostaglandin derivative wherein Z is not a hydroxyl group, it is preferred to convert Z of a fluorine-containing prostaglandin derivative from a hydroxyl group to a different group. A fluorine-containing prostaglandin derivative wherein Z is not a hydroxyl group can be prepared from a phosphorane or its precursor having a group other than a hydroxyl group as Z.

Conversion of a phosphonium salt wherein Z is —NHCOR$^5$ or —NHSO$_2$R$^6$ to a phosphorane is sometimes accompanied by replacement of the hydrogen atom bonded to the nitrogen atom in —NHCOR$^5$ or —NHSO$_2$R$^6$ by a metal ion. Consequently, in such a case, the product of the Wittig reaction of the resulting phosphorane with a lactol also has a metal ion at the corresponding site. The metal ion is attributed to the metal ion (specifically, an alkali metal ion or an alkaline earth metal ion) in the base used for conversion of a phosphonium salt into a phosphorane. The metal ion can eventually be replaced by a hydrogen atom through hydrolysis or other processes.

Examples of the phosphonium salts include, for example, the following compounds. These phosphonium salts yield the corresponding phosphoranes.

(4-Carboxybutyl)triphenylphosphonium bromide;
(4-carboxy-3-oxabutyl)triphenylphosphonium bromide;
[4-(N-methanesulfonyl)carbamoylbutyl] triphenylphosphonium bromide;
[4-(N-benzoyl)carbamoylbutyl]triphenylphosphonium bromide;
(4-carboxybutyl)tri(o-tolyl)phosphonium bromide;
(4-carboxybutyl)tri(m-tolyl)phosphonium bromide; and
(4-carboxybutyl)tri(p-tolyl)phosphonium bromide.

A phosphorane is used usually in an amount of from 0.1 to 20 equivalents, preferably from 1 to 10 equivalents, per equivalent of a lactol. The reaction of a lactol with a phosphorane is classified as the so-called Wittig reaction. Ordinary conditions for the Wittig reaction are applicable to the reaction of a lactol with a phosphorane according to the present invention. In particular, it is preferred to carry out the reaction under basic conditions in an inert solvent. The reaction temperature is usually from −150 to +200° C., preferably from −80° to +100° C.

A base is used usually in an amount of from 1 to 20 equivalents, preferably from 2 to 10 equivalents, per equivalent of a lactol. A base of the proper kind should be used in view of the acidity of the hydrogen atom bonded to the carbon atom at the α-position based on the phosphorus atom of a phosphonium salt as the precursor of a phosphorane and the stability of the resulting phosphorane. Such a base can be selected, for example, from the following bases.

Sodium hydroxide, potassium hydroxide, sodium carbonate, potassium carbonate, sodium methoxide, sodium ethoxide, triethylamine, diisopropylethylamine, pyridine, N-methylmorpholine, 1,5-diazabicyclo[4.3.0]non-5-ene, 1,8-diazabicyclo[5.4.0]undec-7-ene, potassium t-butoxide, lithium amide, sodium amide, potassium amide, lithium diisopropylamide, lithium diethylamide, lithium dicyclohexylamide, lithium isopropylcyclohexylamide, lithium 2,2,6,6-tetramethylpiperidine, lithium bis (trimethylsilyl)amide, sodium diethylamide, sodium bis (trimethylsilyl)amide, potassium 3-aminopropylamide, potassium bis(trimethylsilyl)amide, lithium hydride, sodium hydride, potassium hydride, sodium methylsulfinylmethylide, n-butyllithium, s-butyllithium, t-butyllithium, methyllithium, phenyllithium, lithium naphthalenide, lithium biphenylide and tritylsodium.

Among these bases, potassium carbonate, potassium t-butoxide, lithium amide, sodium amide, potassium amide, lithium diisopropylamide, lithium diethylamide, lithium dicyclohexylamide, lithium isopropylcyclohexylamide, lithium 2,2,6,6-tetramethylpiperidine, lithium bis (trimethylsilyl)amide, sodium diethylamide, sodium bis (trimethylsilyl)amide, potassium 3-aminopropylamide, potassium bis(trimethylsilyl)amide and sodium methylsulfinylmethylide are preferred. Potassium t-butoxide, sodium bis(trimethylsilyl)amide, potassium bis(trimethylsilyl) amide and sodium methylsulfinylmethylide are particularly preferred.

As the inert solvent, an etherial solvent, a hydrocarbon solvent, a polar solvent, an aqueous solvent, an alcoholic solvent or a solvent mixture thereof is preferred. An inert solvent is used usually in an amount of from 5 to 1000 parts by weight, preferably from 10 to 100 parts by weight, per part by weight of a lactol. As specific examples of the etherial solvent, the hydrocarbon solvent and the polar solvent, the etherial solvents, the hydrocarbon solvents and the polar solvents specifically described above for the fluorination are preferred. As the aqueous solvent, water or a solvent mixture of water with an alcoholic solvent is preferred. As the alcoholic solvent, methanol, ethanol, t-butanol and t-amyl alcohol are preferred. Particularly preferred solvents are diethyl ether, THF, 1,2-dimethoxyethane, t-butyl methyl ether and toluene.

Z of the resulting fluorine-containing prostaglandin derivative can be converted into a different kind of Z, if necessary. For example, a fluorine-containing prostaglandin derivative wherein Z is a hydroxyl group can optionally be converted into an ester, a salt of a carboxylic acid, an acyl amide, sulfonamide or a thioester by a conventional method.

For esterification of Z, ordinary methods such as methods disclosed in publications such as "Shinjikken Kagaku Koza 14 Syntheses and reactions of organic compounds (II)" published by Maruzen may be used. Esterification by condensation with an alcohol or a phenol, esterification with an O-alkylating agent, esterification by use of an alkene or an alkyne, esterification with a dialkyl sulfate or a halogenated hydrocarbon may be mentioned.

For conversion into an acyl amide or a sulfonamide, the method of Tithereley et al. (J. Chem. Soc. 85, 1673 (1904)), the method of Lynch et al. (Can. J. Chem. 50, 2143 (1972)), the method of Davidson et al. (J. Am. Chem. Soc. 80, 376 (1958)) and the like can be used. Alternatively, conversion of a carboxylic acid into an acid halide or a reactive ester followed by condensation with an amide or a sulfonamide or reaction of a carboxylic acid with an amine to produce an amide followed by acylation or sulfonylation may be employed.

For conversion of Z into a thioester, methods described in publications such as "Shinjikken Kagaku Koza 14 Syntheses and reactions of organic compounds (III)" published by Maruzen and "protective Groups in Organic Syntheses" written by T. W. Greene and published by J. Wiley & Sons may be employed. For example, a process comprising conversion of a carboxylic acid is converted into an acid halide or a reactive ester and then reacted with a thiol may be employed.

Specific examples of the compound of the formula (I) are given below, and, however, the compound is not limited to these specific examples.

15-Deoxy-15,15-difluoroprostaglandin $F_{2\alpha}$, 15-deoxy-15,15-difluoroprostaglandin $F_{2\alpha}$ methyl ester, 15-deoxy-15,15-difluoroprostaglandin $F_{2\alpha}$ ethyl ester, 15-deoxy-15,15-difluoroprostaglandin $F_{2\alpha}$ isopropyl ester, 16-(3,5-dichlorophenoxy)-15-deoxy-15,15-difluoro-17,18,19,20-tetranorprostaglandin $F_{2\alpha}$ methyl ester, 16-(3,5-dichlorophenoxy)-15-deoxy-15,15-difluoro-17,18,19,20-tetranorprostaglandin $F_{2\alpha}$ ethyl ester, 16-(3,5-dichlorophenoxy)-15-deoxy-15,15-difluoro-17,18,19,20-tetranorprostaglandin $F_{2\alpha}$ isopropyl ester, 16-(3,4-dichlorophenoxy)-15-deoxy-15,15-difluoro-17,18,19,20-tetranorprostaglandin $F_{2\alpha}$ methyl ester, 16-(3,4-dichlorophenoxy)-15-deoxy-15,15-difluoro-17,18,19,20-tetranorprostaglandin $F_{2\alpha}$ ethyl ester, 16-(3,4-dichlorophenoxy)-15-deoxy-15,15-difluoro-17,18,19,20-tetranorprostaglandin $F_{2\alpha}$ isopropyl ester, 16-(3-chlorophenoxy)-15-deoxy-15,15-difluoro-17,18,19,20-tetranorprostaglandin $F_{2\alpha}$ methyl ester, 16-(3-chlorophenoxy)-15-deoxy-15,15-difluoro-17,18,19,20-tetranorprostaglandin $F_{2\alpha}$ ethyl ester, 16-(3-chlorophenoxy)-15-deoxy-15,15-difluoro-17,18,19,20-tetranorprostaglandin $F_{2\alpha}$ isopropyl ester, 16-(3-trifluoromethylphenoxy)-15-deoxy-15,15-difluoro-17,18,19,20-tetranorprostaglandin $F_{2\alpha}$ methyl ester, 16-(3-trifluoromethylphenoxy)-15-deoxy-15,15-difluoro-17,18,19,20-tetranorprostaglandin $F_{2\alpha}$ ethyl ester, 16-(3-trifluoromethylphenoxy)-15-deoxy-15,15-difluoro-17,18,19,20-tetranorprostaglandin $F_{2\alpha}$ isopropyl ester, 16-phenoxy-15-deoxy-15,15-difluoro-17,18,19,20-tetranorprostaglandin $F_{2\alpha}$ methyl ester, 16-phenoxy-15-deoxy-15,15-difluoro-17,18,19,20-tetranorprostaglandin $F_{2\alpha}$ ethyl ester, 16-phenoxy-15-deoxy-15,15-difluoro-17,18,19,20-tetranorprostaglandin $F_{2\alpha}$ isopropyl ester, 17-phenyl-15-deoxy-15,15-difluoro-18,19,20-trinorprostaglandin $F_{2\alpha}$ methyl ester, 17-phenyl-15-deoxy-15,15-difluoro-18,19,20-trinorprostaglandin $F_{2\alpha}$ ethyl ester, 17-phenyl-15-deoxy-15,15-difluoro-18,19,20-trinorprostaglandin $F_{2\alpha}$ isopropyl ester, 15-deoxy-15,15-difluoro-13,14-dihydroprostaglandin $F_{2\alpha}$ methyl ester, 15-deoxy-15,15-difluoro-13,14-dihydroprostaglandin $F_{2\alpha}$ ethyl ester, 15-deoxy-15,15-difluoro-13,14-dihydroprostaglandin $F_{2\alpha}$ isopropyl ester, 16-(3,5-dichlorophenoxy)-15-deoxy-15,15-difluoro-13,14-dihydro-17,18,19,20-tetranorprostaglandin $F_{2\alpha}$ methyl ester, 16-(3,5-dichlorophenoxy)-15-deoxy-15,15-difluoro-13,14-dihydro-17,18,19,20-tetranorprostaglandin $F_{2\alpha}$ ethyl ester, 16-(3,5-dichlorophenoxy)-15-deoxy-15,15-difluoro-13,14-dihydro-17,18,19,20-tetranorprostaglandin $F_{2\alpha}$ isopropyl ester, 16-(3,4-dichlorophenoxy)-15-deoxy-15,15-difluoro-13,14-dihydro-17,18,19,20-tetranorprostaglandin $F_{2\alpha}$ methyl ester, 16-(3,4-dichlorophenoxy)-15-deoxy-15,15-difluoro-13,14-dihydro-17,18,19,20-tetranorprostaglandin $F_{2\alpha}$ ethyl ester, 16-(3,4-dichlorophenoxy)-15-deoxy-15,15-difluoro-13,14-dihydro-17,18,19,20-tetranorprostaglandin $F_{2\alpha}$ isopropyl ester;

16-(3-chlorophenoxy)-15-deoxy-15,15-difluoro-13,14-dihydro-17,18,19,20-tetranorprostaglandin $F_{2\alpha}$ methyl ester, 16-(3-chlorophenoxy)-15-deoxy-15,15-difluoro-13,14-dihydro-17,18,19,20-tetranorprostaglandin $F_{2\alpha}$ ethyl ester, 16-(3-chlorophenoxy)-15-deoxy-15,15-difluoro-13,14-dihydro-17,18,19,20-tetranorprostaglandin $F_{2\alpha}$ isopropyl ester, 16-(3-trifluoromethylphenoxy)-15-deoxy-15,15-difluoro-13,14-dihydro-17,18,19,20-tetranorprostaglandin $F_{2\alpha}$ methyl ester, 16-(3-trifluoromethylphenoxy)-15-deoxy-15,15-difluoro-13,14-dihydro-17,18,19,20-tetranorprostaglandin $F_{2\alpha}$ ethyl ester, 16-(3-trifluoromethylphenoxy)-15-deoxy-15,15-difluoro-13,14-dihydro-17,18,19,20-tetranorprostaglandin $F_{2\alpha}$ isopropyl ester;

16-phenoxy-15-deoxy-15,15-difluoro-13,14-dihydro-17,18,19,20-tetranorprostaglandin $F_{2\alpha}$ methyl ester, 16-phenoxy-15-deoxy-15,15-difluoro-13,14-dihydro-17,18,19,20-tetranorprostaglandin $F_{2\alpha}$ ethyl ester, 16-phenoxy-15-deoxy-15,15-difluoro-13,14-dihydro-17,18,19,20-tetranorprostaglandin $F_{2\alpha}$ isopropyl ester, 17-phenyl-15-deoxy-15,15-difluoro-13,14-dihydro-18,19,20-trinorprostaglandin $F_{2\alpha}$ methyl ester, 17-phenyl-15-deoxy-15,15-difluoro-13,14-dihydro-18,19,20-trinorprostaglandin $F_{2\alpha}$ ethyl ester, 17-phenyl-15-deoxy-15,15-difluoro-13,14-dihydro-18,19,20-trinorprostaglandin $F_{2\alpha}$ isopropyl ester;

15-deoxy-15,15-difluoro-3-oxaprostaglandin $F_{2\alpha}$, 15-deoxy-15,15-difluoro-3-oxaprostaglandin $F_{2\alpha}$ methyl ester, 15-deoxy-15,15-difluoro-3-oxaprostaglandin $F_{2\alpha}$ ethyl ester, 15-deoxy-15,15-difluoro-3-oxaprostaglandin $F_{2\alpha}$ isopropyl ester, 16-(3,5-dichlorophenoxy)-15-deoxy-15,15-difluoro-3-oxa-17,18,19,20-tetranorprostaglandin $F_{2\alpha}$ methyl ester, 16-(3,5-dichlorophenoxy)-15-deoxy-15,15-difluoro-3-oxa-17,18,19,20-tetranorprostaglandin $F_{2\alpha}$ ethyl ester, 16-(3,5-dichlorophenoxy)-15-deoxy-15,15-difluoro-3-oxa-17,18,19,20-tetranorprostaglandin $F_{2\alpha}$ isopropyl ester, 16-(3,4-dichlorophenoxy)-15-deoxy-15,15-difluoro-3-oxa-17,18,19,20-tetranorprostaglandin $F_{2\alpha}$ methyl ester, 16-(3,4-dichlorophenoxy)-15-deoxy-15,15-difluoro-3-oxa-17,18,19,20-tetranorprostaglandin $F_{2\alpha}$ ethyl ester, 16-(3,4-dichlorophenoxy)-15-deoxy-15,15-difluoro-3-oxa-17,18,19,20-tetranorprostaglandin $F_{2\alpha}$ isopropyl ester, 16-(3-chlorophenoxy)-15-deoxy-15,15-difluoro-3-oxa-17,18,19,20-tetranorprostaglandin $F_{2\alpha}$ methyl ester, 16-(3-chlorophenoxy)-15-deoxy-15,15-difluoro-3-oxa-17,18,19,20-tetranorprostaglandin $F_{2\alpha}$ ethyl ester, 16-(3-chlorophenoxy)-15-deoxy-15,15-difluoro-3-oxa-17,18,19,20-tetranorprostaglandin $F_{2\alpha}$ isopropyl ester;

16-(3-trifluoromethylphenoxy)-15-deoxy-15,15-difluoro-3-oxa-17,18,19,20-tetranorprostaglandin $F_{2\alpha}$ methyl ester, 16-(3-trifluoromethylphenoxy)-15-deoxy-15,15-difluoro-3-oxa-17,18,19,20-tetranorprostaglandin $F_{2\alpha}$ ethyl ester, 16-(3-trifluoromethylphenoxy)-15-deoxy-15,15-difluoro-3-oxa-17,18,19,20-tetranorprostaglandin $F_{2\alpha}$ isopropyl ester, 16-phenoxy-15-deoxy-15,15-difluoro-3-oxa-17,18,19,20-tetranorprostaglandin $F_{2\alpha}$ methyl ester, 16-phenoxy-15-deoxy-15,15-difluoro-3-oxa-17,18,19,20-tetranorprostaglandin $F_{2\alpha}$ ethyl ester, 16-phenoxy-15-deoxy-15,15-difluoro-3-oxa-17,18,19,20-tetranorprostaglandin $F_{2\alpha}$ isopropyl ester;

17-phenyl-15-deoxy-15,15-difluoro-3-oxa-18,19,20-trinorprostaglandin $F_{2\alpha}$ methyl ester, 17-phenyl-15-deoxy-15,15-difluoro-3-oxa-18,19,20-trinorprostaglandin $F_{2\alpha}$ ethyl ester, 17-phenyl-15-deoxy-15,15-difluoro-3-oxa-18,19,20-trinorprostaglandin $F_{2\alpha}$ isopropyl ester, 15-deoxy-15,15-difluoro-9-pivaloylprostaglandin $F_{2\alpha}$ methyl ester, 15-deoxy-15,15-difluoro-9-pivaloylprostaglandin $F_{2\alpha}$ ethyl ester, 15-deoxy-15,15-difluoro-9-pivaloylprostaglandin $F_{2\alpha}$ isopropyl ester;

16-(3,5-dichlorophenoxy)-15-deoxy-15,15-difluoro-9-pivaloyl-17,18,19,20-tetranorprostaglandin $F_{2\alpha}$ methyl ester, 16-(3,5-dichlorophenoxy)-15-deoxy-15,15-difluoro-9-pivaloyl-17,18,19,20-tetranorprostaglandin $F_{2\alpha}$ ethyl ester, 16-(3,5-dichlorophenoxy)-15-deoxy-15,15-difluoro-9-pivaloyl-17,18,19,20-tetranorprostaglandin $F_{2\alpha}$ isopropyl ester, 16-(3,4-dichlorophenoxy)-15-deoxy-15,15-difluoro-9-pivaloyl-17,18,19,20-tetranorprostaglandin $F_{2\alpha}$ methyl ester, 16-(3,4-dichlorophenoxy)-15-deoxy-15,15-difluoro-9-pivaloyl-17,18,19,20-tetranorprostaglandin $F_{2\alpha}$ ethyl ester, 16-(3,4-dichlorophenoxy)-15-deoxy-15,15-difluoro-9-pivaloyl-17,18,19,20-tetranorprostaglandin $F_{2\alpha}$ isopropyl ester;

16-(3-chlorophenoxy)-15-deoxy-15,15-difluoro-9-pivaloyl-17,18,19,20-tetranorprostaglandin $F_{2\alpha}$ methyl ester, 16-(3-chlorophenoxy)-15-deoxy-15,15-difluoro-9-pivaloyl-17,18,19,20-tetranorprostaglandin $F_{2\alpha}$ ethyl ester, 16-(3-chlorophenoxy)-15-deoxy-15,15-difluoro-9-pivaloyl-17,18,19,20-tetranorprostaglandin $F_{2\alpha}$ isopropyl ester, 16-(3-trifluoromethylphenoxy)-15-deoxy-15,15-difluoro-9-pivaloyl-17,18,19,20-tetranorprostaglandin $F_{2\alpha}$ methyl ester, 16-(3-trifluoromethylphenoxy)-15-deoxy-15,15-difluoro-9-pivaloyl-17,18,19,20-tetranorprostaglandin $F_{2\alpha}$ ethyl ester, 16-(3-trifluoromethylphenoxy)-15-deoxy-15,15-difluoro-9-pivaloyl-17,18,19,20-tetranorprostaglandin $F_{2\alpha}$ isopropyl ester;

16-phenoxy-15-deoxy-15,15-difluoro-9-pivaloyl-17,18,19,20-tetranorprostaglandin $F_{2\alpha}$ methyl ester, 16-phenoxy-15-deoxy-15,15-difluoro-9-pivaloyl-17,18,19,20-tetranorprostaglandin $F_{2\alpha}$ ethyl ester, 16-phenoxy-15-deoxy-15,15-difluoro-9-pivaloyl-17,18,19,20-tetranorprostaglandin $F_{2\alpha}$ isopropyl ester, 17-phenyl-15-deoxy-15,15-difluoro-9-pivaloyl-18,19,20-trinorprostaglandin $F_{2\alpha}$ methyl ester, 17-phenyl-15-deoxy-15,15-difluoro-9-pivaloyl-18,19,20-trinorprostaglandin $F_{2\alpha}$ ethyl ester, 17-phenyl-15-deoxy-15,15-difluoro-9-pivaloyl-18,19,20-trinorprostaglandin $F_{2\alpha}$ isopropyl ester;

15-deoxy-15,15-difluoro-11-pivaloylprostaglandin $F_{2\alpha}$ methyl ester, 15-deoxy-15,15-difluoro-11-pivaloylprostaglandin $F_{2\alpha}$ ethyl ester, 15-deoxy-15,15-difluoro-11-pivaloylprostaglandin $F_{2\alpha}$ isopropyl ester, 16-(3,5-dichlorophenoxy)-15-deoxy-15,15-difluoro-11-pivaloyl-17,18,19,20-tetranorprostaglandin $F_{2\alpha}$ methyl ester, 16-(3,5-dichlorophenoxy)-15-deoxy-15,15-difluoro-11-pivaloyl-17,18,19,20-tetranorprostaglandin $F_{2\alpha}$ ethyl ester, 16-(3,5-dichlorophenoxy)-15-deoxy-15,15-difluoro-11-pivaloyl-17,18,19,20-tetranorprostaglandin $F_{2\alpha}$ isopropyl ester;

16-(3,4-dichlorophenoxy)-15-deoxy-15,15-difluoro-11-pivaloyl-17,18,19,20-tetranorprostaglandin $F_{2\alpha}$ methyl ester, 16-(3,4-dichlorophenoxy)-15-deoxy-15,15-difluoro-11-pivaloyl-17,18,19,20-tetranorprostaglandin $F_{2\alpha}$ ethyl ester, 16-(3,4-dichlorophenoxy)-15-deoxy-15,15-difluoro-11-pivaloyl-17,18,19,20-tetranorprostaglandin $F_{2\alpha}$ isopropyl ester, 16-(3-chlorophenoxy)-15-deoxy-15,15-difluoro-11-pivaloyl-17,18,19,20-tetranorprostaglandin $F_{2\alpha}$ methyl ester, 16-(3-chlorophenoxy)-15-deoxy-15,15-difluoro-11-pivaloyl-17,18,19,20-tetranorprostaglandin $F_{2\alpha}$ ethyl ester, 16-(3-chlorophenoxy)-15-deoxy-15,15-difluoro-11-pivaloyl-17,18,19,20-tetranorprostaglandin $F_{2\alpha}$ isopropyl ester;

16-(3-trifluoromethylphenoxy)-15-deoxy-15,15-difluoro-11-pivaloyl-17,18,19,20-tetranorprostaglandin $F_{2\alpha}$ methyl ester, 16-(3-trifluoromethylphenoxy)-15-deoxy-15,15-difluoro-11-pivaloyl-17,18,19,20-tetranorprostaglandin $F_{2\alpha}$ ethyl ester, 16-(3-trifluoromethylphenoxy)-15-deoxy-15,15-difluoro-11-pivaloyl-17,18,19,20-tetranorprostaglandin $F_{2\alpha}$ isopropyl ester, 16-phenoxy-15-deoxy-15,15-difluoro-11-pivaloyl-17,18,19,20-tetranorprostaglandin $F_{2\alpha}$ methyl ester, 16-phenoxy-15-deoxy-15,15-difluoro-11-pivaloyl-17,18,19,20-tetranorprostaglandin $F_{2\alpha}$ ethyl ester, 16-phenoxy-15-deoxy-15,15-difluoro-11-pivaloyl-17,18,19,20-tetranorprostaglandin $F_{2\alpha}$ isopropyl ester;

17-phenyl-15-deoxy-15,15-difluoro-11-pivaloyl-18,19,20-trinorprostaglandin $F_{2\alpha}$ methyl ester, 17-phenyl-15-deoxy-15,15-difluoro-11-pivaloyl-18,19,20-trinorprostaglandin $F_{2\alpha}$ ethyl ester, 17-phenyl-15-deoxy-15,15-difluoro-11-pivaloyl-18,19,20-trinorprostaglandin $F_{2\alpha}$ isopropyl ester, 15-deoxy-15,15-difluoroprostaglandin $F_{2\alpha}$ 1,9-lactone, 15-deoxy-15,15-difluoroprostaglandin $F_{2\alpha}$ 1,11-lactone, 16-(3,5-dichlorophenoxy)-15-deoxy-15,15-difluoro-17,18,19,20-tetranorprostaglandin $F_{2\alpha}$ 1,9-lactone;

16-(3,5-dichlorophenoxy)-15-deoxy-15,15-difluoro-17,18,19,20-tetranorprostaglandin $F_{2\alpha}$ 1,11-lactone, 16-(3,4-dichlorophenoxy)-15-deoxy-15,15-difluoro-17,18,19,20-tetranorprostaglandin $F_{2\alpha}$ 1,9-lactone, 16-(3,4-dichlorophenoxy)-15-deoxy-15,15-difluoro-17,18,19,20-tetranorprostaglandin $F_{2\alpha}$ 1,11-lactone, 16-(3-chlorophenoxy)-15-deoxy-15,15-difluoro-17,18,19,20-tetranorprostaglandin $F_{2\alpha}$ 1,9-lactone, 16-(3-chlorophenoxy)-15-deoxy-15,15-difluoro-17,18,19,20-tetranorprostaglandin $F_{2\alpha}$ 1,11-lactone, 16-(3-trifluoromethylphenoxy)-15-deoxy-15,15-difluoro-17,18,19,20-tetranorprostaglandin $F_{2\alpha}$ 1,9-lactone;

16-(3-trifluoromethylphenoxy)-15-deoxy-15,15-difluoro-17,18,19,20-tetranorprostaglandin $F_{2\alpha}$ 1,11-lactone, 16-phenoxy-15-deoxy-15,15-difluoro-17,18,19,20-tetranorprostaglandin $F_{2\alpha}$ 1,9-lactone, 16-phenoxy-15-deoxy-15,15-difluoro-17,18,19,20-tetranorprostaglandin $F_{2\alpha}$ 1,11-lactone, 17-phenyl-15-deoxy-15,15-difluoro-18,19,20-trinorprostaglandin $F_{2\alpha}$ 1,9-lactone, 17-phenyl-15-deoxy-15,15-difluoro-18,19,20-trinorprostaglandin $F_{2\alpha}$ 1,11-lactone;

16-(3,5-dichlorophenoxy)-15-deoxy-15,15-difluoro-17,18,19,20-tetranorprostaglandin $F_{2\alpha}$, 16-(3,4-dichlorophenoxy)-15-deoxy-15,15-difluoro-17,18,19,20-tetranorprostaglandin $F_{2\alpha}$, 16-(3-chlorophenoxy)-15-deoxy-15,15-difluoro-17,18,19,20-tetranorprostaglandin $F_{2\alpha}$, 16-(3-trifluoromethylphenoxy)-15-deoxy-15,15-difluoro-17,18,19,20-tetranorprostaglandin $F_{2\alpha}$;

16-phenoxy-15-deoxy-15,15-difluoro-17,18,19,20-tetranorprostaglandin $F_{2\alpha}$, 17-phenyl-15-deoxy-15,15-difluoro-18,19,20-trinorprostaglandin $F_{2\alpha}$, 15-deoxy-15,15-difluoro-13,14-dihydroprostaglandin $F_{2\alpha}$, 16-(3,5-dichlorophenoxy)-15-deoxy-15,15-difluoro-13,14-dihydro-17,18,19,20-tetranorprostaglandin $F_{2\alpha}$, 16-(3,4-dichlorophenoxy)-15-deoxy-15,15-difluoro-13,14-dihydro-17,18,19,20-tetranorprostaglandin $F_{2\alpha}$;

16-(3-chlorophenoxy)-15-deoxy-15,15-difluoro-13,14-dihydro-17,18,19,20-tetranorprostaglandin $F_{2\alpha}$, 16-(3-trifluoromethylphenoxy)-15-deoxy-15,15-difluoro-13,14-dihydro-17,18,19,20-tetranorprostaglandin $F_{2\alpha}$, 16-phenoxy-15-deoxy-15,15-difluoro-13,14-dihydro-17,18,19,20-tetranorprostaglandin $F_{2\alpha}$, 17-phenyl-15-deoxy-15,15-difluoro-13,14-dihydro-18,19,20-trinorprostaglandin $F_{2\alpha}$, 15-deoxy-15,15-difluoro-3-oxa-prostaglandin $F_{2\alpha}$, 16-(3,5-dichlorophenoxy)-15-deoxy-15,15-difluoro-3-oxa-17,18,19,20-tetranorprostaglandin $F_{2\alpha}$;

16-(3,4-dichlorophenoxy)-15-deoxy-15,15-difluoro-3-oxa-17,18,19,20-tetranorprostaglandin $F_{2\alpha}$, 16-(3-chlorophenoxy)-15-deoxy-15,15-difluoro-3-oxa-17,18,19,20-tetranorprostaglandin $F_{2\alpha}$, 16-(3-trifluoromethylphenoxy)-15-deoxy-15,15-difluoro-13,14-dihydro-3-oxa-17,18,19,20-tetranorprostaglandin $F_{2\alpha}$, 16-phenoxy-15-deoxy-15,15-difluoro-13,14-dihydro-3-oxa-17,18,19,20-tetranorprostaglandin $F_{2\alpha}$, 17-phenyl-15-deoxy-15,15-difluoro-13,14-dihydro-3-oxa-18,19,20-trinorprostaglandin $F_{2\alpha}$;

N-methanesulfonyl-15-deoxy-15,15-difluoroprostaglandin $F_{2\alpha}$ carboxamide, N-methanesulfonyl-16-(3,5-dichlorophenoxy)-15-deoxy-15,15-difluoro-17,18,19,20-tetranorprostaglandin $F_{2\alpha}$ carboxamide, N-methanesulfonyl-16-(3,4-dichlorophenoxy)-15-deoxy-15,15-difluoro-17,18,19,20-tetranorprostaglandin $F_{2\alpha}$ carboxamide, N-methanesulfonyl-16-(3-chlorophenoxy)-15-deoxy-15,15-difluoro-17,18,19,20-tetranorprostaglandin $F_{2\alpha}$ carboxamide, N-methanesulfonyl-16-(3-trifluoromethylphenoxy)-15-deoxy-15,15-difluoro-17,18,19,20-tetranorprostaglandin $F_{2\alpha}$ carboxamide, N-methanesulfonyl-16-phenoxy-15-deoxy-15,15-difluoro-17,18,19,20-tetranorprostaglandin $F_{2\alpha}$ carboxamide, and N-methanesulfonyl-17-phenyl-15-deoxy-15,15-difluoro-18,19,20-trinorprostaglandin $F_{2\alpha}$ carboxamide.

The fluorine-containing prostaglandin derivative of the formula (I) has asymmetric carbon atoms in its structure and thus has various stereoisomers and optical isomers. The fluorine-containing prostaglandin derivatives of the present invention include all of such stereoisomers, optical isomers and their mixtures.

The compounds of the present invention (the fluorine-containing prostaglandin derivatives and their salts) are superior to known naturally occurring $PGF_{2\alpha}$ in the effect of lowering intraocular pressure. They hardly irritate the eye and have very little effect on the ocular tissues such as the cornea, the iris and the conjunctiva. Further, they are unlikely to decompose through metabolic processes such as hydrolysis and oxidation and stable in the body. They also easily penetrate the cornea and are easily absorbed by the eye. For these reasons, they are very useful as medicines. In addition, they solve the problem of the stimulation of melanogenesis by conventional $PGF_{2\alpha}$ derivatives and are compounds which hardly stimulate melanogenesis. Therefore, the medicine of the present invention is effective as a therapeutic agent, particularly for glaucoma or ocular hypertension.

The medicine of the present invention is a pharmaceutical containing the compound of the present invention as an active ingredient and typically applied to the eye, for example, in drops. As its dosage forms, external preparations such as eye drops and ophthalmic ointments and injections are mentioned, and the compounds of the present invention are formulated by using common techniques. For example, in the case of eye drops, isotonicities such as sodium chloride and concentrated glycerine, buffering agents such as sodium phosphate and sodium acetate, surfactants such as polyoxyethylene sorbitane monoolate (hereinafter referred to as polysorbate 80), polyoxyl 40 stearate and polyoxyethylene hydrogenated castor oil, stabilizers such as sodium citrate and sodium edetate and antiseptics such as benzalkonium chloride and paraben are optionally used to prepare the medicine of the present invention. The pH should be within a range acceptable for ocular medicines and is preferably from 4 to 8.

Although the dose depends on the condition and the age of the patient and the dosage form, in the case of an ophthalmic solution, it is applied to the eye at a concentration of 0.0001 to 1% (w/v), preferably from 0.0005 to 0.5% (w/v) once or a couple of times a day.

Now, the present invention will be described in further detail with reference to Examples. However, the present invention is by no means restricted to such specific Examples. In Examples 1 to 21, compounds of the present invention were prepared. Example 22 illustrates formulations of the medicines of the present invention, and in Example 23, a pharmacological tests of medicines of the present invention are presented.

EXAMPLE 1

Preparation of (1S,5R,6R,7R)-2-oxa-7-benzoyloxy-6-[(1E)-4-(3-chlorophenoxy)-3-oxo-1-butenyl]bicyclo[3.3.0]octan-3-one To a solution of 26.5 g of dimethyl 2-oxo-3-(3-chlorophenoxy)propylphosphonate in THF (260 ml), 3.39 g of lithium chloride and 10.9 ml of triethylamine were added under cooling with ice. After 15 minutes of stirring, a solution of 18.1 g of (1S,5R,6R,7R)-6-formyl-7-benzoyloxy-2-oxabicyclo[3.3.0]octan-3-one in methylene chloride (65 ml) was added. After 1 hour of stirring at 0° C., the reaction solution was poured into a 1/1 mixture of saturated aqueous ammonium chloride/ethyl acetate, and the resulting mixture was allowed to separeate. The aqueous layer was extracted with ethyl acetate, and the combined organic layer was dried and concentrated. The concentrate was purified by silica gel column chromatography (hexane/ethyl acetate 1/3–2/1) to obtain 19.8 g of the above-identified compound.

$^1H$ NMR(CDCl$_3$); δ 2.2–2.9(m,6H),4.67(s,2H),5.09(m,1H), 5.34(m,1H),6.56(d,J=15.9 Hz,1H),6.73–6.97(m,4H), 7.18 (m,1H),7.44(m,2H),7.58(m,1H),7.97(m,2H).

EXAMPLE 2

Preparation of (1S,5R,6R,7R)-2-oxa-7-benzoyloxy-6-[(1E)-3,3-difluoro-4-(3-chlorophenoxy)-1-butenyl]bicyclo[3.3.0]octan-3-one To a solution of 5.00 g of the enone prepared in Example 1 in methylene chloride (150 ml), 19.8 g of morpholinosulfur trifluoride was added at 0° C. The resulting mixture was stirred at room temperature for 180 hours, then poured into saturated aqueous sodium bicarbonate and extracted with ethyl acetate. The extract was purified by silica gel column chromatography (hexane/ethyl acetate 2/1) to obtain 3.47 g of the above-identified compound.

$^1H$ NMR(CDCl$_3$): δ 2.2–3.0(m,6H),4.13(m,2H),5.09(m,1H), 5.30(m,1H),5.87(dt,J=15.6,11.2 Hz,1H),6.15(m,1H), 6.72 (m,1H),6.84(m,1H),6.97(m,1H),7.18(m,1H),7.41(m,2H),7.55 (m,1H),7.96(m,2H). $^{19}F$ NMR(CDCl$_3$): −104.1 (m).

EXAMPLE 3

Preparation of (1S,5R,6R,7R)-2-oxa-7-hydroxy-6-[(1E)-3,3-difluoro-4-(3-chlorophenoxy)-1-butenyl]bicyclo[3.3.0]octan-3-one 3.47 g of the fluoride prepared in Example 2 was dissolved in 40 ml of methanol, and 645 mg of potassium carbonate was added. The mixture was stirred at room temperature for 3 hours. After the pH was adjusted to about 7 with acetic acid, water was added, and the mixture was extracted with ethyl acetate. The extract was purified by silica gel column chromatography (hexane/ethyl acetate 1/2–2/3) to obtain 2.69 g of the above-identified compound.

$^1H$ NMR(CDCl$_3$): δ 2.0–2.8(m,6H),4.09–4.21(m,3H), 4.95(m,1H),5.84(dt,J=15.6,11.2 Hz,1H),6.07(m,1H),6.81 (m,1H),6.91(m,1H),7.01(m,1H),7.23(m,1H). $^{19}F$ NMR (CDCl$_3$): −103.7(m).

EXAMPLE 4

Preparation of (1S,5R,6R,7R)-2-oxa-3,7-dihydroxy-6-[(1E)-3,3-difluoro-4-(3-chlorophenoxy)-1-butenyl]bicyclo[3.3.0]octane To a solution of 1.57 g of (1S,5R,6R,7R)-2-oxa-7-hydroxy-6-[(1E)-3,3-difluoro-4-(3-chlorophenoxy)-1-butenyl]bicyclo[3.3.0]octan-3-one prepared in Example 3 in THF (50 ml), a toluene solution (1M, 17.5 ml) of diisobutylaluminum hydride was added at −78° C., and the mixture was stirred for 30 minutes. Water (20 ml) and 1N hydrochloric acid (40 ml) were added, and the mixture was extracted with ethyl acetate. The extract was purified by silica gel column chromatography (hexane/ethyl acetate 1/1–3/2) to obtain 1.26 g of the above-identified compound.

$^1$H NMR(CDCl$_3$): δ 2.0–2.6(m,6H),2.89–3.10(m,1H), 3.98(m,1H),4.18(m,2H),4.66(m,1H),5.57–5.67(m,1H),5.79 (m,1H),6.11(m,1H),6.81(m,1H),6.92(m,1H),6.99(m,1H), 7.22(m,1H). $^{19}$F NMR(CDCl$_3$): −103.4(m).

EXAMPLE 5

Preparation of 16-(3-chlorophenoxy)-15-deoxy- 15, 15-difluoro-17,18,19,20-tetranorprostaglandin F$_{2\alpha}$ isopropyl ester To a solution of 6.21 g of 4-carboxybutyltriphenylphosphonium bromide in THF (80 ml), a toluene solution (0.5M, 56 ml) of potassium bis (trimethylsilyl)amide was added, and the mixture was stirred at room temperature for 30 minutes. A solution of 1.26 g of the lactol prepared in Example 4 in THF (30 ml) was added at −20° C., and the mixture was stirred at room temperature for 1 hour. Water was added to terminate the reaction, and the reaction mixture was washed with diethyl ether. The aqueous layer was acidified and then extracted with ethyl acetate. The extract was dried, and then the solvent was evaporated off to obtain 1.56 g of a crude carboxylic acid.

To a solution of 1.56 g of the carboxylic acid thus obtained in acetone (14 ml), 4.28 g of 1,8-diazabicyclo [5.4.0]undec-7-ene and 5.38 g of 2-iodopropane were added, and the mixture was stirred for 17 hours. The reaction mixture was diluted with ethyl acetate, then washed with saturated aqueous sodium chloride, 3% aqueous citric acid and aqueous sodium bicarbonate, dried and concentrated. The concentrate was purified by silica gel column chromatography (hexane/ethyl acetate 1/1) to obtain 0.91 g of the above-identified compound.

$^1$H NMR(CDCl$_3$): δ 1.22(d,J=6.4 Hz,6H),1.6–2.8(m, 14H), 4.03(m,1H),4.18(t,J=11.7 Hz,2H),4.21(m,1H),4.99 (m,1H), 5.38(m,1H),5.78(dt,J=15.6,11.2 Hz,1H),6.10(m, 1H),6.81 (m,1H),6.92(m,1H),6.98(m,1H),7.21(m,1H). $^{19}$F NMR(CDCl$_3$): −103.3(m).

EXAMPLE 6

Preparation of 16-(3-chlorophenoxy)-15-deoxy-15, 15-difluoro-17,18,19,20-tetranorprostaglandin F$_{2\alpha}$ To a solution of 440 mg of 16-(3-chlorophenoxy)-15-deoxy-15,15-difluoro-17,18,19,20-tetranorprostaglandin F$_{2\alpha}$ isopropyl ester prepared in Example 5 in ethanol (13 ml), 0.2N aqueous sodium hydroxide (11.3 ml) was added, and the mixture was stirred at room temperature for 22 hours. The reaction solution was poured into saturated aqueous sodium bicarbonate and washed with toluene. The reaction solution was adjusted to pH 1 with 2N hydrochloric acid and then extracted with ethyl acetate. The extract was dried and concentrated to obtain 423 mg of the above-identified compound.

$^1$H NMR(CDCl$_3$): δ 1.6–2.5(m,14H),4.04(m,1H), 4.14–4.20(m,3H),5.38(m,2H),5.78(dt,J=15.6,11.2 Hz,1H), 6.09 (m,1H),6.81(m,1H),6.92(m,1H),6.98(m,1H),7.21(m, 1H). $^{19}$F NMR(CDCl$_3$): −103.4(m).

EXAMPLE 7

Preparation of 16-(3-chlorophenoxy)-15-deoxy-15, 15-difluoro-17,18,19,20-tetranorprostaglandin F$_{2\alpha}$ ethyl ester To a solution of 200 mg of 16-(3-chlorophenoxy)-15-deoxy-15,15-difluoro-17,18,19,20-tetranorprostaglandin F$_{2\alpha}$ prepared in Example 6 in acetone (2 ml), 275 mg of 1,8-diazabicyclo[5.4.0]undec-7-ene and 316 mg of iodoethane were added, and the resulting reaction solution was stirred for 5 hours. The reaction solution was diluted with ethyl acetate, then washed with saturated aqueous sodium chloride, 3% aqueous citric acid and aqueous sodium bicarbonate, dried and concentrated. The concentrate was purified by silica gel column chromatography (hexane/ethyl acetate 1/1) to obtain 82 mg of the above-identified compound.

$^1$H NMR(CDCl$_3$); δ 1.25(t,J=7.3 Hz,3H),1.6–2.6(m, 14H), 4.04(m,1H),4.12(q,J=7.3 Hz,2H),4.15–4.21(m,3H), 5.39(m,2H), 5.78(dt,J=15.6,11.2 Hz,1H),6.11(m,1H),6.81 (m,1H),6.92 (m,1H),6.99(m,1H),7.22(m,1H). $^{19}$F NMR (CDCl$_3$): −103.4(m).

EXAMPLE 8

Preparation of 16-(3-chlorophenoxy)-15-deoxy-15, 15-difluoro-17,18,19,20-tetranorprostaglandin F$_{2\alpha}$ methyl ester To a solution of 221 mg of 16-(3-chlorophenoxy)-15-deoxy-15,15-difluoro-17,18,19,20-tetranorprostaglandin F$_{2\alpha}$ in a solvent mixture of methanol (1 ml) and benzene (4 ml), trimethylsilyldiazomethane (10% hexane solution, 2.5 ml) was added, and the resulting reaction solution was stirred for 30 minutes. Acetic acid was added dropwise to terminate the reaction, and the reaction solution was concentrated. The concentrate was purified by silica gel column chromatography (hexane/ethyl acetate 1/1) to obtain 65 mg of the above-identified compound.

$^1$H NMR(CDCl$_3$): δ 1.6–2.5(m,14H),3.66(s,3H),4.04(m, 1H), 4.15–4.21(m,3H),5.39(m,2H),5.78(dt,J=15.6,11.2 Hz,1H), 6.11(m,1H),6.81(m,11H),6.92(m,1H),6.99(m,1H), 7.22(m,1H). $^{19}$F NMR(CDCl$_3$): −103.4(m).

EXAMPLE 9

Preparation of 16-phenoxy-15-deoxy-15,15-difluoro-17,18,19,20-tetranorprostaglandin F$_{2\alpha}$ isopropyl ester The above-identified compound was prepared in the same manners as in Examples 1 to 5 using (1S,5R,6R,7R)-6-formyl-7-benzoyloxy-2-oxabicyclo[3.3.0]octan-3-one and dimethyl 2-oxo-3-phenoxypropylphosphonate.

$^1$H NMR(CDCl$_3$): δ 1.22(d,J=6.4 Hz,6H),1.59(m,1H), 1.66 (m,2H),1.83(m,1H),2.0–2.4(m,7H),2.47(m,1H),4.02 (m,1H), 4.19(t,J=11.5 Hz,2H),4.19(m,1H),4.99(m,1H),5.38 (m,2H),5.80 (dt,J=15.6,11.2 Hz,1H),6.10(m,1H),6.91(m, 2H),7.00(m,1H), 7.30(m,2H). $^{19}$F NMR(CDCl$_3$): −103.7 (m).

The following compounds were prepared in the respective steps in the present Example.

(1S,5R,6R,7R)-2-oxa-7-benzoyloxy-6-[(1E)-4-phenoxy-3-oxo-1-butenyl]bicyclo[3.3.0]octan-3-one $^1$H NMR(CDCl$_3$): δ 2.29(ddd,J=15.6,4.9,0.2 Hz,1H), 2.45–2.51(m,1H),2.60(dt,J=15.6,6.6 Hz,1H),2.83–2.95(m, 3H), 4.67(s,2H),5.08(td,J=4.6,1.7 Hz,1H),5.31(m,1H),6.60 (dd, J=15.6,1.0 Hz,1H),6.84–6.87(m,2H),6.91(dd,J=15.6, 7.8 Hz,1H),6.98(t,J=7.3 Hz,1H),7.25–7.29(m,2H),744 (t,J= 7.3 Hz,2H),7.58(dt,J=7.3,1.2 Hz,1H),7.97(dd,J=8.3, 1.2 Hz,2H).

(1S,5R,6R,7R)-2-oxa-7-benzoyloxy-6-[(1E)-3,3-difluoro-4-phenoxy-1-butenyl]bicyclo[3.3.0]octan-3-one $^1$H NMR(CDCl$_3$): δ 2.2–2.9(m,6H),4.17(t,J=11.5 Hz,2H), 5.09(m,1H),5.29(m,1H),5.89(dt,J=15.6,11.0 Hz,1H),6.15

(m,1H),6.85(d,J=7.8 Hz,2H),6.99(t,J=7.3 Hz,1H),7.27(m, 2H), 7.41(m,2H),7.55(t,J=7.3 Hz,1H),7.97(d,J=7.3 Hz,2H). $^{19}$F NMR(CDCl$_3$): −104.0(m).

(1S,5R,6R,7R)-2-oxa-7-hydroxy-6-[(1E)-3,3-difluoro-4-phenoxy-1-butenyl]bicyclo[3.3.0]octan-3-one $^1$H NMR(CDCl$_3$): δ 2.0–2.8(m,6H),4.09(m,1H),4.20(t, J=11.5 Hz,2H),4.94(m,1H),5.84(dt,J=15.6,11.2 Hz,1H),6.07 (m,1H),6.91(d,J=7.8 Hz,2H),7.02(t,J=7.3 Hz,1H),7.31(m, 2H). $^{19}$F NMR(CDCl$_3$): −103.6(m).

(1S,5R,6R,7R)-2-oxa-3,7-dihydroxy-6-[(1E)-3,3-difluoro-4-phenoxy-1-butenyl]bicyclo[3.3.0]octane $^1$H NMR(CDCl$_3$): δ 1.8–2.9(m,6H),3.96(m,1H),4.19 (t,J= 11.5 Hz,2H),4.60–4.71(m,1H),5.56–5.65(m,1H),5.82 (m,1H),6.11(m,1H),6.91(d,J=8.3 Hz,2H),7.00(m,1H),7.30 (t,J=7.8 Hz,2H). $^{19}$F NMR(CDCl$_3$): −103(m).

EXAMPLE 10

Preparation of 16-phenoxy-15-deoxy-15,15-difluoro- 17,18,19,20-tetranorprostaglandin F$_{2\alpha}$ The above-identified compound was prepared in the same manner as in Example 6 using 16-phenoxy-15-deoxy-15,15-difluoro-17,18,19,20-tetranorprostaglandin F$_{2\alpha}$ isopropyl ester prepared in Example 9.

$^1$H NMR(CDCl$_3$): δ 1.60(m,1H),1.67(m,2H),1.83(m,1H), 2.0–2.5(m,8H),2.47(m,1H),4.03(m,1H),4.18(t,J=11.7 Hz,2H), 4.18(m,1H),5.36(m,2H),5.80(dt,J=15.8,10.5 Hz,1H),6.09 (m,1H),6.91(m,2H),6.99(m,1H),7.29(m,2H). $^{19}$F NMR(CDCl$_3$): −103.7(m).

EXAMPLE 11

Preparation of 16-phenoxy-15-deoxy-15,15-difluoro-17,18,19,20-tetranorprostaglandin F$_{2\alpha}$ ethyl ester The above-identified compound was prepared in the same manner as in Example 7 using 16-phenoxy-15-deoxy-15,15-difluoro-17,18,19,20-tetranorprostaglandin F$_{2\alpha}$ prepared in Example 10.

$^1$H NMR(CDCl$_3$): δ 1.25(t,J=7.2 Hz,3H),1.55–1.75(m, 3H), 1.85(m,1H),2.05–2.50(m,8H),4.01(m,1H),4.12(q,J= 7.2 Hz,2H), 4.20(t,J=11.7 Hz,2H),4.21(m,1H),5.38(m,2H), 5.81(dt,J=11.1, 15.7 Hz,1H),6.10(ddt,J=2.0,9.1,15.7 Hz,1H) ,6.91(m,2H),7.00 (m,1H),7.30(m,2H). $^{19}$F NMR(CDCl$_3$): −103.3(m).

EXAMPLE 12

Preparation of 16-phenoxy-15-deoxy-15,15-difluoro-17,18,19,20-tetranorprostaglandin F$_{2\alpha}$ methyl ester The above-identified compound was prepared in the same manner as in Example 8 using 16-phenoxy-15-deoxy-15,15-difluoro-17,18,19,20-tetranorprostaglandin F$_{2\alpha}$ prepared in Example 10.

$^1$H NMR(CDCl$_3$): δ 1.60(m,1H),1.67(m,2H),1.84(m,1H), 2.0–2.4(m,8H),2.47(m,1H),3.66(s,3H),4.02(m,1H),4.20 (t,J=12.0 Hz,2H),4.20(m,1H),5.38(m,2H),5.80(dt,J=16.4, 10.8 Hz,1H),6.10(m,1H),6.91(m,2H),7.00(m,1H),7.30(m, 2H). $^{19}$F NMR(CDCl$_3$): −103.7(m).

EXAMPLE 13

Preparation of 16-(3,5-dichlorophenoxy)-15-deoxy-15,15-difluoro-17,18,19,20-tetranorprostaglandin F$_{2\alpha}$ isopropyl ester The above-identified compound was prepared in the same manners as in Examples 1 to 5 using (1S,5R,6R,7R)-6-formyl-7-benzoyloxy-2-oxabicyclo[3.3.0]octan-3-one and dimethyl 2-oxo-3-(3,5-dichlorophenoxy)propylphosphonate.

$^1$H NMR(CDCl$_3$): δ 1.23(d,J=6.1 Hz,6H),1.6–2.5(m, 12H), 4.03(m,1H),4.17(t,J=11.4 Hz,2H),4.22(m,1H),5.00 (m,1H),5.39 (t,J=5.0 Hz,2H),5.76(m,1H),6.11(m,1H),6.83 (d,J=1.8 Hz,2H), 7.02(t,J=1.8 Hz,1H). $^{19}$F NMR(CDCl$_3$): −103.5(m).

The following compounds were prepared in the respective steps in the present Example.

(1S,5R,6R,7R)-2-oxa-7-benzoyloxy-6-[(1E)-4-(3,5-dichlorophenoxy)-3-oxo-1-butenyl]bicyclo[3.3.0]octan-3-one $^1$H NMR(CDCl$_3$): δ 2.31(ddd,J=15.6,4.9,2.0 Hz,1H),2.51 (m,1H),2.65(dt,J=15.6,6.5 Hz,1H),2.87–2.98(m,3H),4.67 (s,2H),5.11(dt,J=6.5,2.0 Hz,1H),5.35(m,1H),6.54(d, J=16.1 Hz,1H),6.77(d,J=2.0 Hz,2H),6.92(dd,J=16.1,7.8 Hz,1H), 6.99(t,J=2.0 Hz,1H),7.45(m,2H),7.60(m,1H),7.98(m,2H).

(1S,5R,6R,7R)-2-oxa-7-benzoyloxy-6-[(1E)-3,3-difluoro-4-(3,5-dichlorophenoxy)-1-butenyl]bicyclo[3.3.0] octan-3-one $^1$H NMR(CDCl$_3$): δ 2.2–2.9(m,6H),4.12(m,2H),5.08(m, 1H), 5.31(q,J=6.1 Hz,1H),5.85(m,1H),6.14(dd,J=15.9,7.6 Hz,1H), 6.76(d,J=1.7 Hz,2H),6.98(t,J=1.7 Hz,1H),7.4–7.6 (m,3H), 7.94(m,2H). $^{19}$F NMR(CDCl$_3$): −104(m).

(1S,5R,6R,7R)-2-oxa-7-hydroxy-6-[(1E)-3,3-difluoro-4-(3,5-dichlorophenoxy)-1-butenyl]bicyclo[3.3.0]octan-3-one $^1$H NMR(CDCl$_3$): δ 2.04(m,1H),2.4–2.9(m,5H),4.08(dt, J=6.1,6.4 Hz,1H),4.15(t,J=11.5 Hz,2H),4.95(dt,J=4.4,2.4 Hz, 1H),5.79(dt,J=15.9,11.2 Hz,1H),6.06(ddt,J=15.9,8.0,1.0 Hz, 1H),6.81(d,J=1.7 Hz,2H),7.00(t,J=1.7 Hz,1H). $^{19}$F NMR(CDCl$_3$): −103(m).

(1S,5R,6R,7R)-2-oxa-3,7-dihydroxy-6-[(1E)-3,3-difluoro-4-(3,5-dichlorophenoxy)-1-butenyl]bicyclo[3.3.0] octane $^1$H NMR(CDCl$_3$): δ 1.8–2.9(m,6H),3.97(m,1H),4.15(t, J=12.2 Hz,2H),4.65(m,1H),5.55–5.65(m,1H),5.77(m,1H), 6.07 (m,1H),6.82(m,2H),7.01(m,1H). $^{19}$F NMR(CDCl$_3$): −103.5(m).

EXAMPLE 14

Preparation of (1S,5R,6R,7R)-2-oxa-7-benzoyloxy-6-[4-(3-chlorophenoxy)-13-oxobutyl]bicyclo[3.3.0] octan-3-one 5% Pd-C (580 mg) was suspended in a solution of 4.08 g of the enone prepared in Example 1 in ethyl acetate (80 ml), and the suspension was stirred under a hydrogen atmosphere at room temperature for 2 hours. The reaction mixture was filtered through Celite and then concentrated. The concentrate was purified by silica gel column chromatography (hexane/ethyl acetate 1/1) to obtain 3.89 g of the above-identified compound.

$^1$H NMR(CDCl$_3$): δ 1.68(m,1H),1.81(m,1H),2.13(m,1H), 2.35–2.52(m,3H),2.68(m,1H),2.78–2.95(m,3H),4.56(s,2H), 5.10(dt,J=1.0,6.0 Hz,1H),5.20(ddd,J=2.9,3.3,6.0 Hz,1H), 6.74 (m,1H),6.85(m,1H),6.97(m,1H),7.19(m,1H),7.43(m, 2H),7.55 (m,1H),7.97(m,2H).

EXAMPLE 15

Preparation of 16-(3-chlorophenoxy)-15-deoxy-15, 15-difluoro-13, 14-dihydro-17,18,19,20-tetranorprostaglandin F$_{2\alpha}$ isopropyl ester The above-identified compound was prepared in the same manners as in Examples 2 to 5 using the ketone prepared in Example 14.

$^1$H NMR(CDCl$_3$): δ 1.22(d,J=6.4 Hz,6H),1.43(m,2H), 1.65–1.75(m,4H),1.9–2.5(m,10H),3.95(m,1H),4.10(m,2H), 4.20 (m,1H),5.00(m,1H),5.41(m,2H),6.82(m,1H),6.93(m, 1H),6.99 (m,1H),7.22(m,1H). $^{19}$F NMR(CDCl$_3$): −105.7 (m).

The following compounds were prepared in the respective steps in the present Example.

(1S,5R,6R,7R)-2-oxa-7-benzoyloxy-6-[3,3-difluoro-4-(3-chlorophenoxy)butyl]bicyclo[3.3.0]octan-3-one $^1$H NMR(CDCl$_3$): δ 1.68(m,2H),2.2–2.5(m,6H),2.72(m, 1H), 2.94(dd,J=18.3,10.7 Hz,1H),4.11(t,J=11.5 Hz,2H),5.12 (dt, J=5.7,1.0 Hz,1H),5.27(m,1H),6.78(ddd,J=5.9,2.5,1.7 Hz,1H), 6.90(t,J=2.2 Hz,1H),7.01(m,1H),7.21(t,J=8.1 Hz,1H),7.44 (t,J=7.7 Hz,2H),7.54(m,1H),7.99(m,2H). $^{19}$F NMR(CDCl$_3$): −106.1(m).

(1S,5R,6R,7R)-2-oxa-7-hydroxy-6-[3,3-difluoro-4-(3-chlorophenoxy)butyl]bicyclo[3.3.0]octan-3-one $^1$H NMR(CDCl$_3$): δ 1.55–1.68(m,2H),1.89(m,1H), 2.1–2.6(m,6H),2.85(dd,J=18.8,11.2 Hz,1H),4.05(m,1H), 4.10(m,2H),4.98(ddd,J=7.1,6.8,2.2 Hz,1H),6.81(ddd,J=8.3, 1.7,1.0 Hz,1H),6.92(t,J=2.2 Hz,1H),7.01(m,1H),7.23(t, J=8.3 Hz,1H). $^{19}$F NMR(CDCl$_3$): −106.0(m).

EXAMPLE 16

Preparation of 16-(3-chlorophenoxy)-15-deoxy-15, 15-difluoro-13,14-dihydro-17,18,19,20-tetranorprostaglandin F$_{2\alpha}$ The above-identified compound was prepared in the same manner as in Example 6 using 16-(3-chlorophenoxy)-15-deoxy-15,15-difluoro-13,14-dihydro-17,18,19,20-tetranorprostaglandin F$_{2\alpha}$ isopropyl ester prepared in Example 15.

$^1$H NMR(CDCl$_3$): δ 1.41(m,2H),1.65–2.40(m,14H),3.95 (m,1H),4.10(t,J=11.6 Hz,2H),4.17(m,1H),5.40(m,2H),6.81 (m,1H),6.92(m,1H),7.00(m,1H),7.22(m,1H). $^{19}$F NMR (CDCl$_3$): −105.8(m).

EXAMPLE 17

Preparation of 16-(3-chlorophenoxy)-15-deoxy-15, 15-difluoro-13,14-dihydro-17,18,19,20-tetranorprostaglandin F$_{2\alpha}$ methyl ester The above-identified compound was prepared in the same manner as in Example 8 using 16-(3-chlorophenoxy)-15-deoxy-15,15-difluoro-13,14-dihydro-17,18,19,20-tetranorprostaglandin F$_{2\alpha}$ prepared in Example 16.

$^1$H NMR(CDCl$_3$): δ 1.42(m,2H),1.7–2.4(m,14H),3.67 (s,3H),3.95(m,1H),4.11(t,J=11.5 Hz,2H),4.20(m,1H),5.41 (m,2H),6.81(m,1H),6.93(m,1H),7.00(m,1H),7.23(m,1H). $^{19}$F NMR(CDCl$_3$): −105.8(m).

EXAMPLE 18

Preparation of 16-phenoxy-15-deoxy-15,15-difluoro-13,14-dihydro-17,18,19,20-tetranorprostaglandin F$_{2\alpha}$ isopropyl ester The above-identified compound was prepared in the same manners as in Examples 1, 14, 2, 3, 4 and 5 using (1S,5R, 6R,7R)-6-formyl-7-benzoyloxy-2-oxabicyclo[3.3.0]octan-3-one and dimethyl 2-oxo-3-phenoxy-propylphosphonate.

$^1$H NMR(CDCl$_3$): δ 1.23(d,J=6.4 Hz,6H),1.4–2.5(m, 18H), 3.95(m,1H),4.10–4.94(m,3H),5.00(m,1H),5.42(m, 2H),6.92 (m,2H),7.01(m,1H),7.31(m,2H). $^{19}$F NMR (CDCl$_3$): −105.7(m).

The following compounds were prepared in the respective steps in the present Example.

(1S,5R,6R,7R)-2-oxa-7-benzoyloxy-6-(4-phenoxy-3-oxobutyl)bicyclo[3.3.0]octan-3-one $^1$H NMR(CDCl$_3$): δ 1.74(m,2H),2.13(m,1H),2.32–2.52 (m,3H),2.66(m,1H),2.80–2.93(m,3H),4.57(s,2H),5.09(m, 1H), 5.20(m,1H),6.85(d,J=7.8 Hz,2H),6.99(t,J=7.3 Hz,1H), 7.28 (m,2H),7.43(m,2H),7.55(t,J=7.3 Hz,1H),7.98(d,J=7.3 Hz,2H).

(1S,5R,6R,7R)-2-oxa-7-benzoyloxy-6-(3,3-difluoro-4-phenoxybutyl)bicyclo[3.3.0]octan-3-one $^1$H NMR(CDCl$_3$): δ 1.67(m,2H),2.18–2.54(m,6H),2.72 (m,1H),2.94(dd,J=18.3,10.5 Hz,1H),4.13(t,J=11.5 Hz,2H), 5.11 (m,1H),5.26(m,1H),6.89(d,J=7.8 Hz,2H),7.01(t,J=7.3 Hz,1H), 7.30(m,2H),7.44(m,2H),7.56(m,1H),7.99(d,J=7.3 Hz,2H). $^{19}$F NMR(CDCl$_3$): −105.9(m).

(1S,5R,6R,7R)-2-oxa-7-hydroxy-6-(3,3-difluoro-4-phenoxybutyl)bicyclo[3.3.0]octan-3-one $^1$H NMR(CDCl$_3$); δ 1.47–1.68(m,2H),1.89(m,1H), 2.0–2.2 (m,3H),2.32(dt,J=15.1,5.9 Hz,1H),2.51–2.60(m,2H) ,2.84(dd, J=18.8,11.0 Hz,1H),4.09(m,1H),4.13(t,J=11.5 Hz,2H),4.98 (m,1H),6.92(d,J=8.3 Hz,2H),7.02(t,J=7.3 Hz,1H),7.32(t, J=7.8 Hz,2H). $^{19}$F NMR(CDCl$_3$): −105.9 (m).

(1S,5R,6R,7R)-2-oxa-3,7-dihydroxy-6-(3,3-difluoro-4-phenoxybutyl)bicyclo[3.3.0]octane $^1$H NMR(CDCl$_3$): δ 1.4–2.5(m,10H),3.95(m,1H),4.12(t, J=11.5 Hz,2H),4.68(m,1H),5.54–5.67(m,1H),6.92(d,J=7.8 Hz, 2H),7.01(t,J=7.3 Hz,1H),7.31(t,J=7.8 Hz,2H). $^{19}$F NMR (CDCl$_3$): −105.6(m).

EXAMPLE 19

Preparation of 16-phenoxy-15-deoxy-15,15-difluoro-13,14-dihydro-17,18,19,20-tetranorprostaglandin F$_{2\alpha}$ The above-identified compound was prepared in the same manner as in Example 6 using 16-phenoxy-15-deoxy-15,15-difluoro-13,14-dihydro-17,18,19,20-tetranorprostaglandin F$_{2\alpha}$ isopropyl ester prepared in Example 18.

$^1$H NMR(CDCl$_3$): δ 1.4–2.4(m,18H),3.96(m,1H),4.12(t, J=11.7 Hz,2H),4.17(m,1H),5.40(m,2H),6.92(m,2H),7.00(m, 1H), 7.30(m,2H). $^{19}$F NMR(CDCl$_3$): −105.7(m).

EXAMPLE 20

Preparation of 16-phenoxy-15-deoxy-15,15-difluoro-13,14-dihydro-17,18,19,20-tetranorprostaglandin F$_{2\alpha}$ ethyl ester The above-identified compound was prepared in the same manner as in Example 7 using 16-phenoxy-15-deoxy-15,15-difluoro-13,14-dihydro-17,18,19,20-tetranorprostaglandin F$_{2\alpha}$ prepared in Example 19.

$^1$H NMR(CDCl$_3$): δ 1.25(t,J=7.3 Hz,3H),1.4–2.7(m, 18H), 3.95(m,1H),4.09–4.18(m,5H),5.41(m,2H),6.92(m, 2H),7.00 (m,1H),7.30(m,2H). $^{19}$F NMR(CDCl$_3$): −105.7 (m).

EXAMPLE 21

Preparation of 16-phenoxy-15-deoxy-15,15-difluoro-13,14-dihydro-17,18,19,20-tetranorprostaglandin F$_{2\alpha}$ methyl ester The above-identified compound was prepared in the same manner as in Example 8 using 16-phenoxy-15-deoxy-15,15- difluoro-13,14-dihydro-17,18,19,20-tetranorprostaglandin $F_{2\alpha}$ prepared in Example 19.

$^1$H NMR(CDCl$_3$): δ 1.4–2.6(m,18H),3.66(s,3H),3.95(m,1H), 4.10–4.19(m,3H),5.41(m,2H),5.76(m,1H),6.92(m,2H), 7.00 (m,1H),7.31(m,2H). $^{19}$F NMR(CDCl$_3$): −105.7(m).

EXAMPLE 22 (FORMULATION EXAMPLE)

Typical formulations of an ophthalmic solution and an ophthalmic ointment containing 16-phenoxy-15-deoxy-15,15-difluoro-17,18,19,20-tetranorprostaglandin $F_{2\alpha}$ methyl ester (hereinafter referred to as Compound A) prepared in Example 12 are given below.

1) Ophthalmic Solution 100 ml

| | |
|---|---|
| Compound A | 10 mg |
| Concentrated glycerine | 2500 mg |
| Polysorbate 80 | 2000 mg |
| Sodium dihydrogenphosphate dihydrate | 200 mg |
| Sterilized pure water | appropriate amount |
| 1N hydrochloric acid or 1N sodium hydroxide | appropriate amount |
| pH | 6.0 |

Based on the above formulation, 0.001% (w/v), 0.005% (w/v), 0.05% (w/v) and 0.1% (w/v) ophthalmic solutions can be prepared by varying the amount of compound A and optionally varying the amounts of the additives.

Moreover, based on the above-formulation, 0.001% (w/v), 0.005% (w/v), 0.01% (w/v), 0.05% (w/v) and 0.1% (w/v) ophthalmic solutions of 16-(3-chlorophenoxy)-15-deoxy-15,15-difluoro-17,18,19,20-tetranorprostaglandin $F_{2\alpha}$ methyl ester (hereinafter referred to as Compound B) prepared in Example 8, 16-phenoxy-15-deoxy-15,15-difluoro-13,14-dihydro-17,18,19,20-tetranorprostaglandin $F_{2\alpha}$ methyl ester (hereinafter referred to as Compound C) prepared in Example 21 and 16-phenoxy-15-deoxy-15,15-difluoro-17,18,19,20-tetranorprostaglandin $F_{2\alpha}$ isopropyl ester (hereinafter referred to as Compound D) prepared in Example 9 can be prepared by using compounds B, C and D instead of compound A and optionally varying the amounts of the additives.

2) Ophthalmic Ointment 100 g

| | |
|---|---|
| Compound A | 0.1 g |
| Liquid paraffin | 20 g |
| White soft paraffin | 77.9 g |
| Purified lanolin | 2 g |

Based on the above formulation, similar opthalmic ointments can be prepared by using compounds B, C and D instead of compound A.

The formulation of a ophthalmic solution containing Latanoprost which was used as a comparative compound is shown below.

| Ophthalmic solution 100 ml | |
|---|---|
| Latanoprost | 10 mg |
| Concentrated glycerine | 2500 mg |
| Polysorbate 80 | 2000 mg |
| Sodium dihydrogenphosphate dihydrate | 200 mg |
| Sterilized pure water | appropriate amount |
| 1N hydrochloric acid or 1N sodium hydroxide | appropriate amount |
| pH | 6.0 |

Based on the above formulation, a 0.1% (w/v) ophthalmic solution of Latanoprost can be prepared by varying the amount of Latanoprost and optionally varying the amounts of the additives.

EXAMPLE 23 (PHARMACOLOGICAL TESTS)

The effects of compounds of the present invention on intraocular pressure and melanogenesis were investigated to find their usefulness as medicines for an ocular disease. Eye irritations caused by them were assessed in accordance with the method of Fukui et al. ("Gendai-no-rinsho", Vol. 4, 277–289 (1970)), and they were found to be irritant to the eye as little as Latanoprost.

1) Effects on Intraocular Pressure

The effects of single application and two-week repeated application of compounds of the present invention to the eye were studied in accordance with the method disclosed in a report of a study on the effect of the tromethamine salt and the isopropyl ester of $PGF_{2\alpha}$ on intraocular pressure in crab-eating macaques (Exp. Eye Res., 61, 677–683 (1995)).

(a) Single Application Test (Method)

Crab-eating macaques weighing from 2.5 to 7.5 kg (3–10 years old) were used in the test. The intraocular pressures were measured just before and 4, 6 and 8 hours after application of the test compounds under ketamine anesthasia (5–10 mg/kg, intramuscular administration) by means of an air-puff applanation tonometer.

(Results)

Table 1 shows the resulting changes in intraocular pressure with time after application of 20 μl of 0.01% (w/v) and 0.1% (w/v) ophthalmic solutions containing compounds A, B, C or D, in relation to the initial intraocular pressure (the intraocular pressure just before application). The results of application of 0.01% (w/v) and 0.1% (w/v) ophthalmic solutions containing Latanoprost, which is known as a therapeutic agent for glaucoma are also shown in Table 1. In the square brackets are the numbers of subjects.

TABLE 1

| | | | Change in ocular pressure after application (mmHg) | | |
|---|---|---|---|---|---|
| | | | 4 hours | 6 hours | 8 hours |
| Compound A | (0.01%) | [7] | −1.7 | −2.3 | −2.3 |
| | (0.1%) | [8] | −2.6 | −3.0 | −3.1 |
| Compound B | (0.01%) | [10] | −0.9 | −1.0 | −1.0 |
| | (0.1%) | [9] | −1.3 | −1.4 | −2.0 |
| Compound C | (0.01%) | [9] | −0.6 | −1.2 | −2.0 |
| | (0.1%) | [9] | −1.0 | −0.4 | −2.0 |
| Compound D | (0.01%) | [12] | −0.1 | −0.8 | −1.3 |
| | (0.1%) | [12] | −0.8 | −1.6 | −2.3 |
| Latanoprost | (0.01%) | [5] | −0.4 | −1.2 | −0.6 |
| | (0.1%) | [8] | −0.8 | −1.3 | −0.8 |

As is evident from Table 1, the intraocular pressure had already started to decrease 4 hours after the application of compounds of the present invention and was still decreasing even 8 hours after the application. Compound A lowered the intraocular pressure twice as much as Latanoprost did 6 hours after application, and about 4 times as much 8 hours after application.

This proves that the compound of the present invention has a long-lasting effect of lowering intraocular pressure.

(b) Two-week Repeated Application Test (Method)

Crab-eating macaques weighing from 2.4 to 5.6 kg (3 to 8 years old) were used in the test. A 20 μl of a test ophthalmic solution was applied to one of the eyes of each macaque, and an equal volume of the corresponding vehicle solution (which was of the same formulation as the ophthalmic solution containing the test compound but did not contain the test compound) was applied to the other eye once a day for 14 consecutive days. The intraocular pressure was measured under ketamine anesthasia (5–10 mg/kg, intramuscular administration) by means of an air-puff applanation tonometer.

(Results)

Table 2 illustrates the resulting difference in intraocular pressure between the right and left eyes [(the intraocular pressure of an eye treated with an ophthalmic solution containing a test compound)—(the intraocular pressure of an eye treated with the corresponding vehicle solution)] 6 hours after application of a 0.01% (w/v) or 0.1% (w/v) ophthalmic solution containing compound D or a 0.1% (w/v) ophthalmic solution containing compound A or B on the 1st, 3rd, 7th, 10th and 14th days. The results of application of a 0.1% (w/v) ophthalmic solution containing Latanoprost, which is known as a therapeutic medicine for glaucoma are also shown in Table 2. In the square brackets are the numbers of subjects.

represented in relation to the amount of melanin in the absence of the test compound.

$$\text{Melanin content } (\%) = \frac{(A_s + B_s)/P_s}{(A_c + B_c)/P_c} \times 100$$

$A_c$: Absorbance of the culture medium in the absence of a test compound
$B_c$: Absorbance of cell solution in the absence of a test compound
$P_c$: The amount of protein in a cell solution in the absence of a test compound
$A_s$: Absorbance of the culture medium in the presence of a test compound
$B_s$: Absorbance of the cell solution in the presence of a test compound
$P_s$: The amount of protein in the cell solution in the presence of a test compound

TABLE 2

| | | | Difference in intraocular pressure between the right and left eyes (mmHg) [(Intraocular pressure of the eye treated with test compound) – (Intraocular pressure of the eye treated with vehicle solution)] | | | | |
|---|---|---|---|---|---|---|---|
| | | | 1st day | 3rd day | 7th day | 10th day | 14th day |
| Compound A | (0.1%) | [7] | −0.5 | −2.7 | −3.4 | −3.3 | −2.6 |
| Compound B | (0.1%) | [7] | −0.5 | −2.5 | −3.2 | −2.8 | −1.9 |
| Compound D | (0.01%) | [7] | −2.1 | −2.8 | −3.0 | −2.2 | −1.9 |
| | (0.1%) | [7] | −1.6 | −4.4 | −3.9 | −2.7 | −2.4 |
| Latanoprost | (0.1%) | [7] | −0.6 | −2.1 | −1.7 | −0.7 | −0.3 |

As is evident from Table 2, the intraocular pressure had remarkably decreased since the 3rd day from the start of the application of compounds of the present invention and kept low till the 14th day. Compound D lowered intraocular pressure about 2 to 8 times as much as Latanoprost did. When the intraocular pressures were measured, no turbid cornea, abnormal conjunctiva vessels, conjunctivoma or secretions were observed.

This proves that the compound of the present invention has an excellent effect of lowering intraocular pressure.

2) Effects on Melanogenesis

The effect of compounds of the present invention on melanogenesis was investigated by using B16 pigment cells in accordance with a report of a study on the effect of pyrroloquinoline quinone on expression of mRNA of tyrosinase, which is involved in melanogenesis (Life Sci., 56, 1707–1713 (1995)).

(Method)

To a B16 pigment cell culture ($2 \times 10^3$ cells/ml) preincubated at 37° C. under 5% $CO_2$ for 24 hours, a test compound was added, and the culture was incubated at 37° C. under 5% $CO_2$ for 48 hours. After renewal of the culture medium and addition of the test compound, the cell culture was incubated at 37° C. under 5% $CO_2$ for another 48 hours. The B16 pigment cells were separated from the culture medium and dissolved in a 0.1N sodium hydroxide- 10% triton-X mixed solution, and the absorbances of the culture medium and the cell solution (wavelength 415 nm) were measured.

The gross amounts of melanin in the culture medium and the cell solution were determined from a calibration chart prepared by using synthetic melanin standard solutions. The amount of protein in the culture medium was measured, and the melanin content was given by the following equation and (Results)

Table 3 illustrates the effect of addition of the free forms (carboxylic acids) of Compounds A, B and C on melanogenesis by B16 pigment cells. The results of addition of the free form (a carboxylic acid) of Latanoprost, which is known as a therapeutic medicine for glaucoma are also shown in Table 3. The free form of Compound D is the same as that of Compound A.

TABLE 3

| | Concentration | | |
|---|---|---|---|
| | 1 $\mu$M | 10 $\mu$M | 100 $\mu$M |
| Compound A | 102% | 113% | 111% |
| Compound B | 110% | 122% | 107% |
| Compound C | 107% | 116% | 127% |
| Latanoprost | 109% | 136% | 224% |

As is evident from Table 3, compounds of the present invention did not have much effect and, the melanin contents in the presence of 100 $\mu$M of them were only about 1.1 to 1.3 times higher than that in the absence of them. On the other hand, when Latanoprost was added at concentrations of 10 $\mu$M and 100 $\mu$M, the melanin contents were about 1.4 times and about 2.2 times, respectively, higher than that in its absence.

This proves that compounds of the present invention have little effect on melanogenesis and do not cause iridal pigmentation when applied repeatedly.

The results of the pharmacological tests clearly indicate that the compounds of the present invention are useful as long-lasting therapeutic medicines for glaucoma, are hardly irritant to the eye and have little effect on melanogenesis.

What is claimed is:

1. A fluorine-containing prostaglandin derivative of the following formula (1) or a salt thereof:

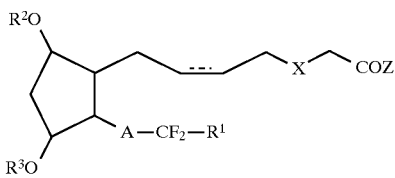

wherein A is an ethylene group, a vinylene group, an ethynylene group, —OCH$_2$— or —SCH$_2$—, R$^1$ is a substituted or unsubstituted aryloxyalkyl group, each of R$^2$ and R$^3$ which are independent of each other, is a hydrogen atom or an acyl group, or forms a single bond together with Z, X is —CH$_2$—, —O— or —S—, Z is —OR$^4$, —NHCOR$^5$, —NHSO$_2$R$^6$ or —SR$^7$, or forms a single bond together with R$^2$ or R$^3$, each of R$^4$, R$^5$, R$^6$ and R$^7$ which are independent of one another, is a hydrogen atom, an alkyl group, an alkenyl group, an alkynyl group, a cycloalkyl group, an aryl group or an aralkyl group, and a dual line consisting of solid and broken lines is a single bond, a cis-double bond or a trans-double bond.

2. The compound according to claim 1, wherein R$^1$ is a phenoxymethyl group, a 3,5-dichlorophenoxymethyl group or a 3-chlorophenoxymethyl group.

3. The compound according to claim 1, which is 16-phenoxy-15-deoxy-15,15-difluoro-17,18,19,20-tetranorprostaglandin F$_{2\alpha}$, 16-(3-chlorophenoxy)-15-deoxy-15,15-difluoro-17,18,19,20-tetranorprostaglandin F$_{2\alpha}$, 16-phenoxy-15-deoxy-15,15-difluoro-13,14-dihydro-17,18,19,20-tetranorprostaglandin F$_{2\alpha}$ or an alkyl ester or a salt thereof.

4. A medicine containing the compound according to claim 1 as an active ingredient.

5. The medicine according to claim 4, which is a preventive or therapeutic medicine for an eye disease.

6. The medicine according to claim 5, wherein the eye disease is glaucoma or ocular hypertension.

7. The medicine according to claim 4, 5 or 6, wherein A is an ethylene group or a vinylene group.

8. The medicine according to claim 4, 5 or 6, wherein X is —CH$_2$—.

9. The medicine according to claim 4, 5 or 6, wherein both R$^2$ and R$^3$ are hydrogen atoms.

10. The medicine according to claim 4, 5 or 6, wherein Z is —OR$^4$.

11. The medicine according to claim 9, wherein R$^1$ is a phenoxymethyl group, a 3,5-dichlorophenoxymethyl group or a 3-chlorophenoxymethyl group.

12. A medicine containing 16-phenoxy-15-deoxy-15,15-difluoro-17,18,19,20-tetranorprostaglandin F$_{2\alpha}$, 16-(3-chlorophenoxy)-15-deoxy-15,15-difluoro-17,18,19,20-tetranorprostaglandin F$_{2\alpha}$, 16-phenoxy-15-deoxy-15,15-difluoro-13,14-dihydro-17,18,19,20-tetranorprostaglandin F$_{2\alpha}$ or an alkyl ester or salt thereof as an active ingredient.

13. The medicine according to claim 12, which is a preventive or therapeutic medicine for an eye disease.

14. The medicine according to claim 13, wherein the eye disease is glaucoma or ocular hypertension.

* * * * *